「 
US011168062B2

(12) United States Patent
Chang et al.

(10) Patent No.: US 11,168,062 B2
(45) Date of Patent: Nov. 9, 2021

(54) **COMPOUNDS FOR THE TREATMENT OF *CLOSTRIDIUM DIFFICILE* INFECTION**

(71) Applicant: University of Notre Dame du Lac, South Bend, IN (US)

(72) Inventors: Mayland Chang, Granger, IN (US); Shahriar Mobashery, Granger, IN (US); Derong Ding, South Bend, IN (US)

(73) Assignee: University of Notre Dame du Lac, South Bend, IN (US)

( * ) Notice: Subject to any disclaimer, the term of this patent is extended or adjusted under 35 U.S.C. 154(b) by 5 days.

(21) Appl. No.: 16/332,311

(22) PCT Filed: Sep. 12, 2017

(86) PCT No.: PCT/US2017/051185
§ 371 (c)(1),
(2) Date: Mar. 11, 2019

(87) PCT Pub. No.: WO2018/049404
PCT Pub. Date: Mar. 15, 2018

(65) Prior Publication Data
US 2019/0210984 A1 Jul. 11, 2019

Related U.S. Application Data

(60) Provisional application No. 62/393,202, filed on Sep. 12, 2016.

(51) Int. Cl.
| | | |
|---|---|---|
| *C07D 271/06* | (2006.01) |
| *C07D 413/04* | (2006.01) |
| *C07D 413/12* | (2006.01) |
| *A61P 31/04* | (2006.01) |
| *C07D 413/10* | (2006.01) |
| *A61K 9/20* | (2006.01) |
| *A61K 9/00* | (2006.01) |
| *A61K 9/12* | (2006.01) |
| *A61K 9/48* | (2006.01) |

(52) U.S. Cl.
CPC .......... *C07D 271/06* (2013.01); *A61K 9/0014* (2013.01); *A61K 9/0019* (2013.01); *A61K 9/12* (2013.01); *A61K 9/2027* (2013.01); *A61K 9/2059* (2013.01); *A61K 9/4866* (2013.01); *A61P 31/04* (2018.01); *C07D 413/04* (2013.01); *C07D 413/10* (2013.01); *C07D 413/12* (2013.01)

(58) Field of Classification Search
None
See application file for complete search history.

(56) References Cited

U.S. PATENT DOCUMENTS

| 5,179,111 A | 1/1993 | Biere et al. |
| 6,277,872 B1 | 8/2001 | Brenner et al. |
| 6,737,248 B2 | 5/2004 | Kunsch et al. |
| 2005/0004005 A1 | 1/2005 | Kasibhatla et al. |
| 2008/0280876 A1 | 11/2008 | Hobson et al. |
| 2011/0086797 A1 | 4/2011 | Dworkin |
| 2011/0207704 A1 | 8/2011 | Cusack et al. |
| 2014/0200226 A1 | 7/2014 | Chakrabarti et al. |

FOREIGN PATENT DOCUMENTS

| EP | 1501515 B1 | 11/2005 |
| WO | 2003007955 A2 | 1/2003 |
| WO | 2003040112 A1 | 5/2003 |
| WO | 2003087044 A2 | 10/2003 |
| WO | 2003087045 A1 | 10/2003 |
| WO | 2003087046 A1 | 10/2003 |
| WO | 2004048319 A1 | 6/2004 |
| WO | 2005115382 A1 | 12/2005 |
| WO | 2007085451 A2 | 8/2007 |
| WO | 2008097428 A2 | 8/2008 |
| WO | 2009041972 A1 | 4/2009 |
| WO | 2009082398 A1 | 7/2009 |
| WO | 2011151618 A2 | 12/2011 |
| WO | WO2016049586 | * 3/2016 |

OTHER PUBLICATIONS

Bruniera et al., The use of vancomycin with its therapeutic and aderse effects: a review. European Review for Medical and Pharmacological Sciences, 2015, 19, 694-700.*
Surawicz et al., Guidlines for Diagnosis, Treatment, and Prevention of Clostridium difficile Infections. The American Journal of Gastroenterology, 2013, 108, 478-498.*
Corsaro, A., "The Role of the Hydrogen Bonding in Cycloadditions of Benzonitrile Oxide with Cyanophenols." Tetrahedron, vol. 52, No. 23, 1996, pp. 7885-7892.
International Search Report and Written Opinion of the ISA/US dated Jan. 27, 2016 in International Application No. PCT/US2015/052474; 11 pgs.
International Search Report and Written Opinion of the ISA/US dated Nov. 22, 2017 in International Application No. PCT/US2017/051185; 8pgs.

(Continued)

*Primary Examiner* — Po-Chih Chen
(74) *Attorney, Agent, or Firm* — Haukaas Fortius PLLC; Michael H. Haukaas

(57) ABSTRACT

*Clostridium difficile* infection (CDI) is a public health threat that results in 14,000 annual deaths in the United States. Challenges involve the production of CDI spores that can remain dormant for years and the production of toxins that damage the gut. Current therapies for CDI include vancomycin and metronidazole, but neither inhibits spore or toxin production. Thus, recurrence of infection occurs in 25% of patients and there are no antibiotics that are effective for multiple recurrences. We describe oxadiazoles with activity against *C. difficile*, including the highly virulent NAP1/027 strain with increased production of toxins A and B, as well as the additional binary toxin. Oxadiazole 2 is poorly absorbed, thus advantageously achieving high concentrations in the gut. The compound targets peptidoglycan synthesis and inhibits vegetative cells, spores, and toxin production.

2 Claims, 4 Drawing Sheets

(56) References Cited

OTHER PUBLICATIONS

Janardhanan et al., "In Vitro and In Vivo Synergy of the Oxadiazole Class of Antibacterials with b-Lactams," Antimicrob. Agents Chemother., 60(9):5581-5588, Sep. 2016.
Janardhanan et al., "The Oxadiazole Antibacterials," Curr Opin Microbiol., 33:13-17, Oct. 2016.
Mathur et al., "Activity of RBx 11760, A Novel Biaryl Oxazolidinone, Against Clostridium difficile," J Antimicrob Chemother., 66(5): 1087-1095, May 2011.
Meisel et al., "An Oxidiazole with Activity Clostridium difficile and High Concentrations in the Gut," Dept. of Chemistry and Biochemistry, Univ. of Notre Dame, MECC 2016—Poster 1, Oct. 2016, 1 pg.
Nerurkar, et al., "Synthesis and Study of Thiocarbanilides Derived from 2-(4' Aminophenyl) Thiazoles and 4-(4', AmInophenyl) Thiazoles for in vitro Antituberculosis Activity-1," Bulletin of Haffkine Institute, 8(1):27-32, 1980.
O'Daniel et al., "Discovery of a New Class of Non-β-lactam Inhibitors of Penicillin-Binding Proteins with Gram-Positive Antibacterial Activity," J Am Chem Soc., 136(9):3664-3672, Mar. 2014.
Pachhamia, et al., "Studies on 2,5-Disubstituted-1,3,4-oxadiazoles. Part—I. Preparation and Antimicrobial Activity of 2-Aryl-5-(4'-benzenesulphonamidophenyl)/(4'-pyridy1)-1,3,4-oxadiazoles," J Indian Chem Soc., 66(4): 250-251, 1989.
Patil, et al., "Synthesis of Some Sulphanilamido-Benzo-thiazolyl Thiazole Derivatives $a_i$ Antibacterial Agents," J Indian Chem Soc., 56(12):1243-1245, 1979.
Pavagadhi, et al., "Synthesis and Antimicrobial Activity of Some New 3-aryl-5-( m-phenoxyphenyl)isoxazoles," Oriental J Chem., 17(2):311-314 (STN Abstract attached), 2001, (CAPLUS printout only).
Spink et al., "Structure-Activity Relationship for the Oxadiazole Class of Antibiotics," J. Med. Chem., 58(3):1380-1389, Jan. 2015.
Vosooghi et al., "Syntheses of Substituted 1,3,4-Oxadiazole, 1,3,4-Thiadiazole and 1,2,4-Triazole Derivatives as Potential Antimicrobial Agents," Journal of Sciences, Islamic Republic of Iran, 16(2):145-151, Spring 2005.
Zhou, T., "Hypervalent iodine in synthesis. 75. A convenient synthesis of oxadiazoles by palladium-catalyzed carbonylation and cyclization of diaryliodonium salts and amidoximes." Synthetic Communications, 32(6), 2002, pp. 887-891.

\* cited by examiner

| Pharmacokinetic Parameters | | |
|---|---|---|
| Administration Route | iv | po |
| Dose (mg/kg) | 20 | 20 |
| $AUC_{0-last}$ (μg·min/mL) | 1146 | 42 |
| $AUC_{0-\infty}$ (μg·min/mL) | 1149 | 44 |
| $C_{max}$ (μg/mL) | - | 0.30 |
| $T_{max}$ (h) | - | 1 |
| CL (mL/min/kg) | 17.4 | - |
| $V_d$ (L/kg) | 1.8 | - |
| $t_{1/2}$ (h) | $t_{1/2\ dist}$ 0.14  $t_{1/2\ elim}$ 1.2 | $t_{1/2\ abs}$ 0.78  $t_{1/2\ dist}$ 0.84  $t_{1/2\ elim}$ 1.1 |
| F (%) | - | 3.8 |

COMPOUNDS FOR THE TREATMENT OF CLOSTRIDIUM DIFFICILE INFECTION

RELATED APPLICATIONS

This application is a National Stage filing under 35 U.S.C. § 371 of International Application No. PCT/US2017/051185 filed Sep. 12, 2017, which claims priority under 35 U.S.C. § 119(e) to U.S. Provisional Patent Application No. 62/393,202, filed Sep. 12, 2016, which applications are incorporated herein by reference.

GOVERNMENT SUPPORT

This invention was made with government support under Grant No. AI090818 awarded by the National Institutes of Health. The government has certain rights in the invention.

BACKGROUND OF THE INVENTION

Clostridium difficile is a Gram-positive spore-forming anaerobic bacterium that causes life-threatening diarrhea, resulting in 250,000 infections per year that require hospitalization and 14,000 annual deaths in the United States alone. C. difficile infection (CDI) is associated with the use of antibiotic therapy, where disruption of the intestinal flora allows for C. difficile colonization. C. difficile produces two toxins, toxin A (TcdA) and toxin B (TcdB), which damage epithelial tissue and promote inflammation that results in rapid fluid loss and diarrhea. Some strains, such as BI/NAP1/027, a highly virulent strain that has spread widely, have increased production of toxins A and B, as well as the additional binary toxin or CDT. This strain is responsible for 31% of the hospital-acquired CDIs. The BI/NAP1/027 strain has also been described in the community, causing 19% of community-associated CDIs. The current antibiotics used to treat CDI are vancomycin, metronidazole, and fidaxomicin. Fidaxomicin is a macrolide that is minimally absorbed, it inhibits RNA synthesis and it has a narrower spectrum of activity for gut microbes. However, treatment failure with fidaxomicin is 12% and lower efficacy is observed with fidaxomicin in BI/NAP1/027 CDIs. Metronidazole contains a nitroimidazole group that is metabolized to a toxic radical species that damages bacterial DNA. Metronidazole has high oral bioavailability, resulting in relative low concentrations in the colon that while approaching MIC are thought to contribute toward resistance development and reduced efficacy in moderate to severe CDI. Vancomycin is poorly absorbed and has demonstrated better efficacy than metronidazole, however metronidazole is used in many countries as first-line therapy because of its low cost and due to the risk of vancomycin-resistant enterococci. As a result, vancomycin is recommended only for severe or complicated CDIs.

One of the most challenging issues in management of CDIs is the recurrence. About 25% of patients treated with vancomycin, metronidazole, or fidaxomicin have recurrence of the infection, and there are no antibiotics that are effective for multiple recurrences. The only option for patients with multiple recurrent CDIs is fecal transplantation, however safety issues are a concern and fecal donor recruitment, preparation and administration by nasogastric tube or enema make it impractical. Another challenge with CDIs is the production of spores that are dormant for months to years. The spores are not susceptible to non-chlorine cleaning agents such as detergent or hydrogen peroxide and are insensitive to most antibiotics. Metronidazole and vancomycin are not active against C. difficile spores at 8× or 80× minimally-inhibitory concentration (MIC). Another difficulty in treating CDIs is the production of toxins: the enterotoxin TcdA, the cytotoxin TCdB, and the binary toxin CDT. These toxins cause changes that disrupt tight junctions and loosen the epithelial barrier, as well as induce the release of inflammatory mediators, which result in inflammation and neutrophil accumulation that lead to destruction of the intestinal epithelium. Neither vancomycin nor metronidazole inhibit toxin production at 8× MIC. Surotomycin, a lipopeptide antibiotic that causes membrane depolarization, is in phase III clinical trials for treatment of CDI. However, surotomycin is not active against spores nor inhibits toxin production.

Accordingly, new antibiotics are needed with low oral bioavailability that can achieve high concentrations in the gastrointestinal track. The optimal antibiotic for CDIs would reduce C. difficile vegetative cells, as well as inhibit toxins and spores, and at the same time would not encourage microbial resistance or affect the host microbiota. In addition, the antibiotic should not cause adverse events in the host. It is extremely challenging for an antibiotic to meet all these criteria, therefore new antibiotics for treating CDIs are urgently needed.

SUMMARY

The discovery of oxadiazole ND-421 (compound 1) provided a compound having potent activity against methicillin-resistant Staphylococcus aureus (MRSA). ND-421 has 97% oral bioavailability, low clearance, and a long terminal half-life of 18.6 hours, and has efficacy in mouse models of MRSA infection. ND-421 also has excellent absorption, therefore, it would not be useful to treat CDIs. Disclosed herein is oxadiazole 2, a compound that is poorly absorbed and inhibits C. difficile vegetative cells, as well as spores and toxin production. We document that oxadiazole 2 has better efficacy than vancomycin in the mouse C. difficile model of recurrent infection. Oxadiazole 2 and related compounds disclosed herein can therefore be useful for the treatment of CDI.

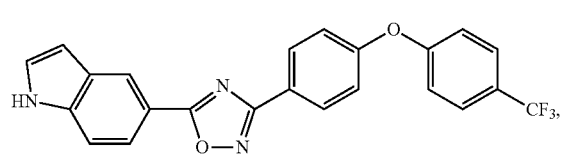

ND-421

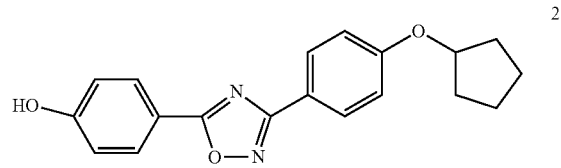

Accordingly, this disclosure provides a compound of Formula (I):

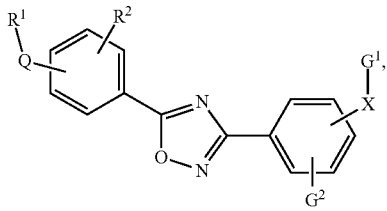

(I)

wherein

Q and X are each independently O, NH, N($C_1$-$C_4$(alkyl)), $CH_2$, or —(C=O)—;

$G^1$ is ($C_3$-$C_8$)cycloalkyl;

$R^1$ is H, OH, $SO_2$($C_1$-$C_4$(alkyl)), ($C_1$-$C_8$)alkyl, or ($C_3$-$C_8$)cycloalkyl; and $R^2$ and $G^2$ are each independently H, OH, halo, alkoxy, alkyl, amino, nitro, carboxyl, or —(C=O)$NH_2$; or $R_1$ is optionally bonded to $R^2$ to form a heterocycle;

wherein ($C_1$-$C_8$)alkyl and ($C_3$-$C_8$)cycloalkyl are saturated or optionally unsaturated, and wherein ($C_1$-$C_8$)alkyl and ($C_3$-$C_8$)cycloalkyl are optionally substituted with 1-3 substituents, wherein each substituent is independently halogen, oxo, hydroxy, alkoxy, $C_1$-$C_4$(alkyl), trifluoromethyl, trifluoromethoxy, or amino;

with the proviso that when $G^1$ is cyclopentyl, a bromocyclopentenyl, a bromocyclohexenyl, or a 4-aminocyclohexyl, $R^1$ is not H or allyl, $R^2$ is not H, or Q or X are not O, and with the proviso that when $R^1$ is bonded to $R^2$ to form an indole moiety, Q is not O;

or a pharmaceutically acceptable salt or solvate thereof.

Additionally, a method is disclosed for treating a *Clostridium difficile* bacterial infection comprising administering to a subject in need thereof an effective amount of a compound of Formula (A), wherein the compound is not substantially absorbed by the gastrointestinal tract where the bacteria to be treated is present, and wherein Formula (A) is:

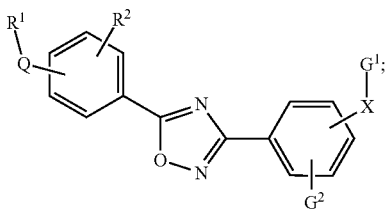

(A)

wherein

Q and X are each independently O, NH, N($C_1$-$C_4$(alkyl)), $CH_2$, or —(C=O)—;

$R^1$ and $G^1$ are each independently H, OH, $SO_2$($C_1$-$C_4$(alkyl)), aryl, heterocycle, ($C_1$-$C_8$)alkyl, or ($C_3$-$C_8$)cycloalkyl; and $R^2$ and $G^2$ are each independently H, OH, halogen, hydroxy, alkoxy, alkyl, amino, nitro, carboxyl, or —(C=O)$NH_2$; or $R^1$ is optionally bonded to $R^2$ to form a heterocycle;

wherein ($C_1$-$C_8$)alkyl and ($C_3$-$C_8$)cycloalkyl are saturated or optionally unsaturated, and wherein aryl, heterocycle, ($C_1$-$C_8$)alkyl and ($C_3$-$C_8$)cycloalkyl are optionally substituted with 1-3 substituents, wherein each substituent is independently halogen, oxo, hydroxy, alkoxy, $C_1$-$C_4$(alkyl), trifluoromethyl, trifluoromethoxy, or amino; or a pharmaceutically acceptable salt or solvate thereof.

The invention provides novel compounds of Formula I-V, intermediates for the synthesis of compounds of Formula I-V, as well as methods of preparing compounds of Formula I-V. The invention also provides compounds of Formula I-V that are useful as intermediates for the synthesis of other useful compounds. The invention provides for the use of compounds of Formula I-V for the manufacture of medicaments useful for the treatment of bacterial infections in a mammal, such as a human.

The invention provides for the use of the compositions described herein for use in medical therapy. The medical therapy can be treating bacterial infections, for example, an infection by a gram-positive spore-forming anaerobic bacterium. The invention also provides for the use of a composition as described herein for the manufacture of a medicament to treat a bacterial infection in a mammal, for example, *C. difficile* infection in a human. The medicament can include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1A:
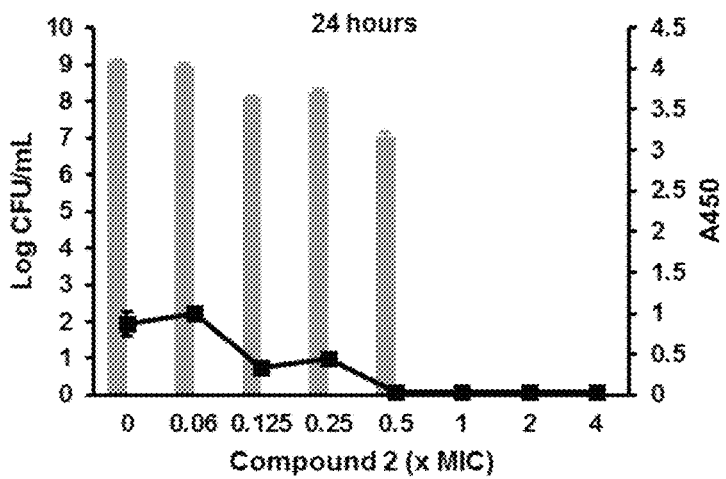
FIG. 1A-1C. Oxadiazole 2 inhibits *C. difficile* vegetative cells, spores, and toxin production. *C. difficile* ATCC43255 was inoculated with serial two-fold dilutions of oxadiazole or metronidazole, and plated after 24 (A), 48 (B), and 72 (C) hours for vegetative cells and spore counts. The culture supernatant was analyzed for TcdA and TcdB toxins by ELISA.

*Clostridium difficile* infection is an urgent public health threat that results in 14,000 annual deaths in the United States alone. The high recurrence rate and the inability of current antibiotics to treat multiple recurrent infections requires urgent need for new therapeutics. We describe the discovery of new oxadiazoles that inhibit vegetative cells, spores, and toxin production. The compounds are poorly absorbed and achieve high concentrations in the gut. The oxadiazoles show better efficacy than vancomycin in a mouse model of recurrent *C. difficile* infection.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* $14^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the end-points of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

The terms "treating", "treat" and "treatment" include (i) inhibiting the disease, pathologic or medical condition or arresting its development; (ii) relieving the disease, pathologic or medical condition; and/or (iii) diminishing symptoms associated with the disease, pathologic or medical condition. Thus, the terms "treat", "treatment", and "treating" include lowering, stopping, or reversing the progression or severity of the condition or symptoms being treated. As such, the term "treatment" can include medical, therapeutic, and/or prophylactic administration, as appropriate.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

In general, a "substituent" refers to an organic group as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, arylalkyloxy groups, oxo(carbonyl) groups, carboxyl groups including carboxylic acids, carboxylates, and carboyxlate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR', OC(O)N(R')$_2$, CN, CF$_3$, OCF$_3$, R', O, S, C(O), S(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$NHC(O)R', N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted.

"Halo" or "halogen" includes fluoro, chloro, bromo, and iodo.

The terms "carbocyclic" and "carbocycle" denote a ring structure wherein the atoms of the ring are carbon. In some embodiments, the carbocycle has 3 to 8 ring members, whereas in other embodiments the number of ring carbon atoms is 4, 5, 6, or 7.

The term "alkoxy" refers to the group alkyl-O—, where alkyl is as defined herein. Examples of alkoxy groups include, but are not limited to, methoxy, ethoxy, n-propoxy, iso-propoxy, n-butoxy, tert-butoxy, sec-butoxy, n-pentoxy, n-hexoxy, 1,2-dimethylbutoxy, and the like. The alkoxy can be unsubstituted or substituted as described for alkyl groups.

The term "amine" includes primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R3N wherein each R is independently selected, such as trialkylamines, dialkylarylamines, alkyldiarylamines, triarylamines, and the like. The term "amine" also includes ammonium ions as used herein.

An "amino" group is a substituent of the form —NH$_2$, —NHR, —NR$_2$, —NR$_3^+$, wherein each R is an independently selected substituent such as alkyl, optionally including protonated forms of each. Accordingly, any compound substituted with an amino group can be viewed as an amine.

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 30 carbon atoms, for example, about 6-10 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described for alkyl groups (below).

The term "heterocycle" refers to a saturated or partially unsaturated ring system, containing at least one heteroatom selected from the group oxygen, nitrogen, silicon, and sulfur, and optionally substituted with one or more groups as defined for the term "substituted". A heterocycle can be a monocyclic, bicyclic, or tricyclic group. Such heterocycles may also be aromatic. Therefore, "heteroaryls" are a subset of heterocycles. A heterocycle group also can contain an oxo group (=O) or a thioxo (=S) group attached to the ring.

Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholinyl, piperazinyl, piperidinyl, pyrazolidinyl, pyrazolinyl, pyrrolidine, pyrroline, quinuclidine, tetrahydrofuranyl, and thiomorpholine.

The term "heteroaryl" refers to a monocyclic, bicyclic, or tricyclic ring system containing one, two, or three aromatic rings and containing at least one nitrogen, oxygen, or sulfur atom in an aromatic ring. The heteroaryl can be unsubstituted or substituted, for example, with one or more, and in particular one to three, substituents, as described in the definition of "substituted". Typical heteroaryl groups contain 2-20 carbon atoms in the ring skeleton in addition to the one or more heteroatoms. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as $NH_4^+$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein.

Embodiments of the Invention

Various embodiments herein disclose a compound of Formula (I):

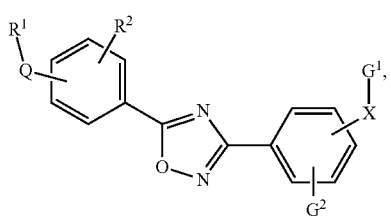

wherein

Q and X are each independently O, NH, N($C_1$-$C_4$(alkyl)), $CH_2$, or —(C=O)—;

$G^1$ is ($C_3$-$C_8$)cycloalkyl;

$R^1$ is H, OH, $SO_2$($C_1$-$C_4$(alkyl)), ($C_1$-$C_8$)alkyl, or ($C_3$-$C_8$)cycloalkyl; and $R^2$ and $G^2$ are each independently H, OH, halo, alkoxy, alkyl, amino, nitro, carboxyl, or —(C=O)$NH_2$; or $R^1$ is optionally bonded to $R^2$ to form a heterocycle, where Q is optionally a direct bond and —$R^1$—$R^2$— forms a 5-6 membered optionally unsaturated ring containing one, two, or three heteroatoms;

wherein ($C_1$-$C_8$)alkyl and ($C_3$-$C_8$)cycloalkyl are saturated or optionally unsaturated, and wherein ($C_1$-$C_8$)alkyl and ($C_3$-$C_8$)cycloalkyl are optionally substituted with 1-3 substituents, wherein each substituent is independently halogen, oxo, hydroxy, alkoxy, $C_1$-$C_4$(alkyl), trifluoromethyl, trifluoromethoxy, or amino;

or a pharmaceutically acceptable salt or solvate thereof.

In various embodiments, Formula (I) includes the proviso that when $G^1$ is cyclopentyl, a bromocyclopentenyl, a bromocyclohexenyl, or a 4-aminocyclohexyl, $R^1$ is not H or allyl, $R^2$ is not H, or Q or X are not O. In further embodiments, Formula (I) can include the proviso that when $R^1$ is bonded to $R^2$ to form an indole moiety, Q is not O. Furthermore, any one or more elements recited for a formula herein may also be explicitly excluded from an embodiment to more particularly claim the scope of the invention.

Various embodiments of alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. Representative substituted alkyl groups can be substituted one or more times with any of the groups listed above, or for example, amino, hydroxy, cyano, carboxy, nitro, thio, alkoxy, and halogen groups.

Various embodiments of cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4-, 2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups.

In some embodiments, Formula (I) is a compound of Formula (II):

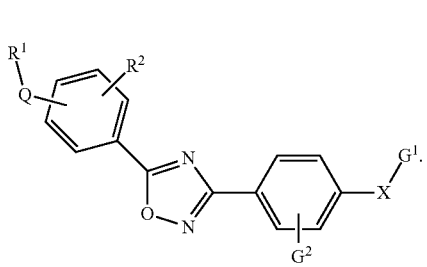
(II)

The group Q can be ortho, meta, or para to the bond of its phenyl ring to the oxadiazole moiety. Furthermore, the group $R^2$ can be ortho, meta, or para to the bond of its phenyl ring to the oxadiazole moiety provided that Q is not in that same position.

In other embodiments, Formula (I) is a compound of Formula (III):

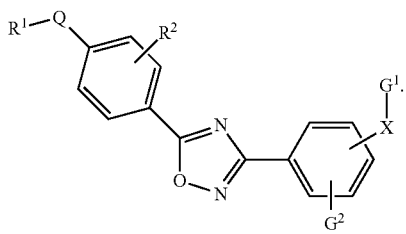
(III)

The group X can be ortho, meta, or para to the bond of its phenyl ring to the oxadiazole moiety. Furthermore, the group $G^2$ can be ortho, meta, or para to the bond of its phenyl ring to the oxadiazole moiety provided that X is not in that same position.

In yet other embodiments, Formula (I) is a compound of Formula (IV):

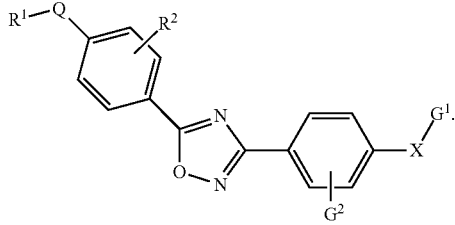
(IV)

In various embodiments, the groups $R^2$ and $G^2$ can be ortho or meta to the bond of its phenyl ring to the oxadiazole moiety.

In additional embodiments of Formula (I) is a compound of Formula (V):

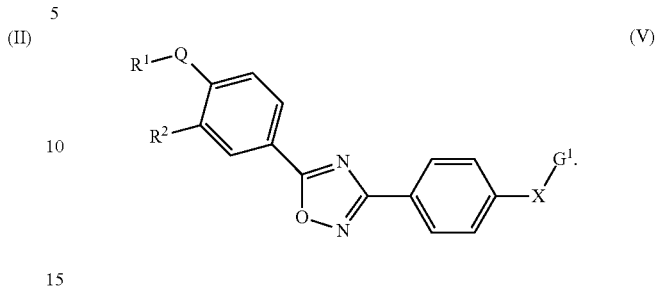
(V)

In various embodiments of the disclosed formulas, $G^2$ is H. In other embodiments $R^2$ is H. In yet other embodiments, $R^2$ is H and $G^2$ is H. In some embodiments X is O and $G^1$ is cyclopropyl, cyclobutyl, cyclopentyl, cyclohexyl, or cycloheptyl. In additional embodiments, $R^1$ is bonded to $R^2$ to form a 5- or 6-membered heteroaryl moiety. Examples include, but are not limited to, a benzimidazole, a benzofuran, a benzotriazole, or a benzoxazole. In various other embodiments, a compound of the disclosed formulas is an optically active compound (i.e., scalemic or substantially optically pure). In other embodiments of the disclosed formulas, Q is N, NH, N($C_1$-$C_4$(alkyl)), C, CH, $CH_2$, or —(C=O)—. For example, when $R^1$ is bonded to $R^2$ and Q is N, the moiety formed can be a quinoline, or if Q is CH, the moiety formed can be a naphthalene. In another example. If Q is C and $R^1$ is an unsaturated alkyl, the substituent formed can be an acetylene. In some particular embodiments, the compound of Formula (I) can be one of compounds i-viii:

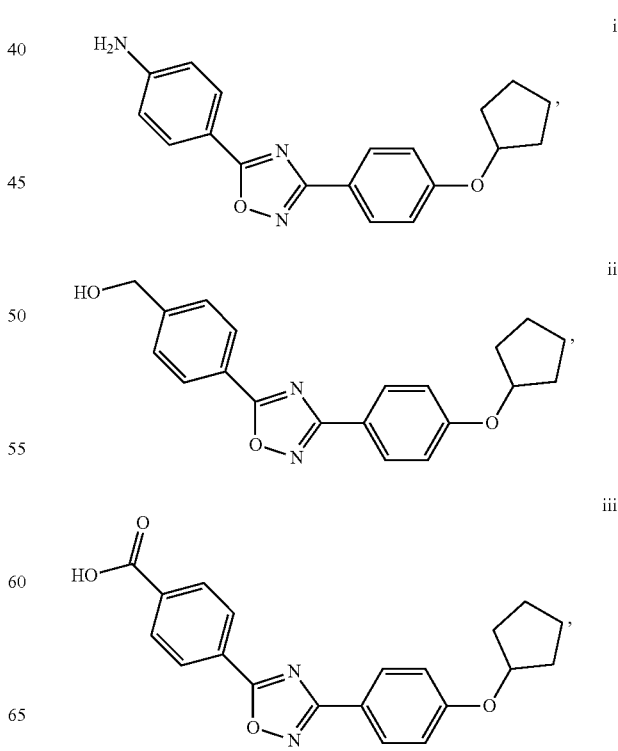

-continued iv
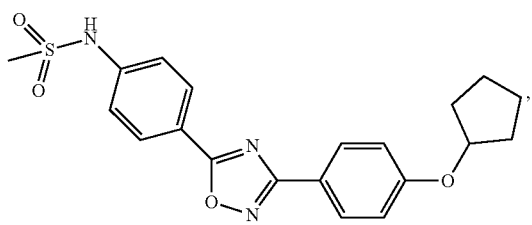

v
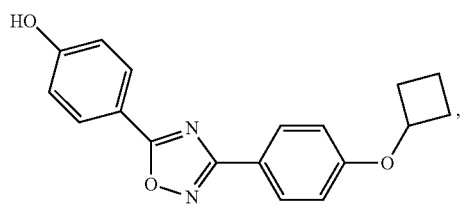

vi
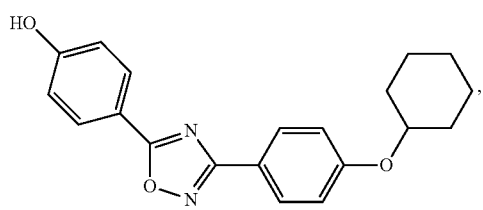

vii
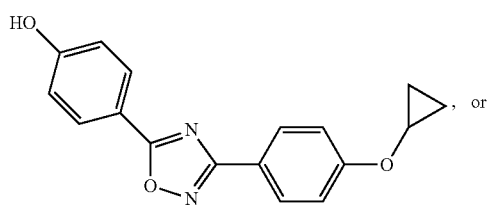, or viii
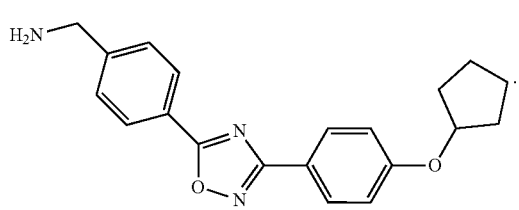

In various embodiments, a pharmaceutical composition comprises any compound disclosed herein, or comprises a compound of any of Formulas I-V, and a pharmaceutically acceptable diluent or carrier.

Additionally, this disclosure provides a method of treating a *Clostridium difficile* bacterial infection comprising administering to a subject in need thereof an effective amount of a compound of Formula (A), wherein the compound is not substantially absorbed (or is substantially not absorbed) by the gastrointestinal tract where the bacteria to be treated is present, and wherein Formula (A) is:

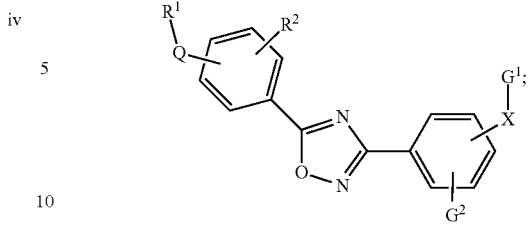

(A)

wherein
Q and X are each independently O, NH, N($C_1$-$C_4$(alkyl)), $CH_2$, or —(C=O)—;

$R^1$ and $G^1$ are each independently H, OH, $SO_2$($C_1$-$C_4$(alkyl)), aryl, heterocycle, ($C_1$-$C_8$)alkyl, or ($C_3$-$C_8$)cycloalkyl; and $R^2$ and $G^2$ are each independently H, OH, halogen, hydroxy, alkoxy, alkyl, amino, nitro, carboxyl, or —(C=O)$NH_2$; or $R^1$ is optionally bonded to $R^2$ to form a heterocycle, where Q is optionally a direct bond and —$R^1$—$R^2$— forms a 5-6 membered optionally unsaturated ring containing one, two, or three heteroatoms;

wherein ($C_1$-$C_8$)alkyl and ($C_3$-$C_8$)cycloalkyl are saturated or optionally unsaturated, and wherein aryl, heterocycle, ($C_1$-$C_8$)alkyl and ($C_3$-$C_8$)cycloalkyl are optionally substituted with 1-3 substituents, wherein each substituent is independently halogen, oxo, hydroxy, alkoxy, $C_1$-$C_4$(alkyl), trifluoromethyl, trifluoromethoxy, or amino;

or a pharmaceutically acceptable salt or solvate thereof.

Embodiments of the disclosed methods include compounds of Formula (A) that are compounds of Formula (B):

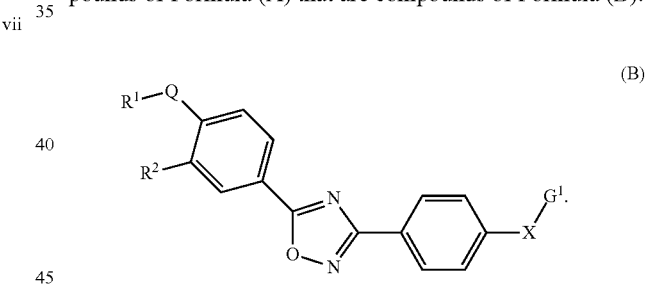

(B)

Embodiments of this disclosure include compounds that are administered orally (po). In various embodiments for the treatment of a *Clostridium difficile* bacterial infection, less than 30 percent of the compound is absorbed by the gastrointestinal tract where the bacteria to be treated is present, and wherein absorption is measured, for example, at 24 hours after administration. In other embodiments, less than 25 percent, less than 20 percent, less than 15 percent, less than 10 percent, less than 5 percent, less than 3 percent, or less than 2.5 percent of the compound is absorbed by the gastrointestinal tract where the bacteria to be treated is present. The administration can be enteral administration, for example, oral, sublingual, or rectal. An ordinary person skilled in the art of drug metabolism or pharmacokinetics would, for example, administer a disclosed compound to an animal by po, then take blood samples at various time points for analysis of the compound present in the sample and determine various pharmacokinetic parameters, such as a calculation to determine how much of a disclosed compound was absorbed and how much additional compound should be administered.

In yet other embodiments, the compound is one of compounds i-viii, and/or one of compounds ix-xxii, or any other compound described or illustrated herein:
ix
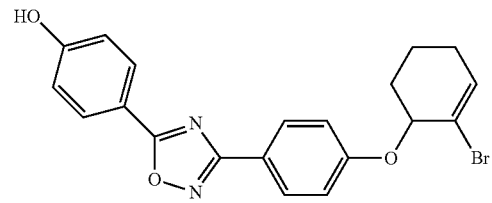
x
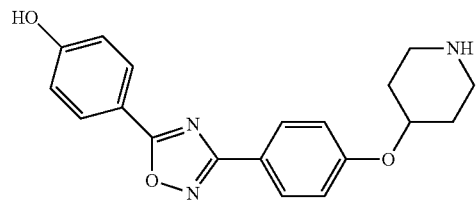
xi
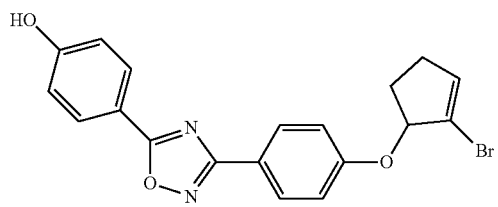
xii
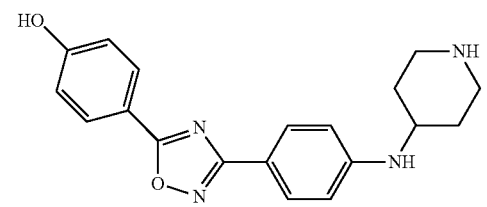
xiii
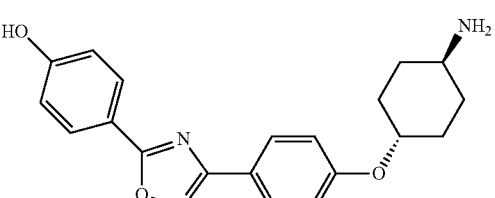
xiv
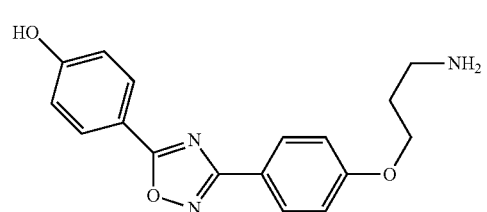
xv
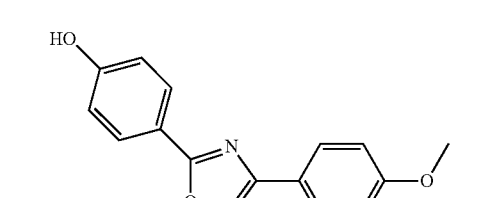
xvi
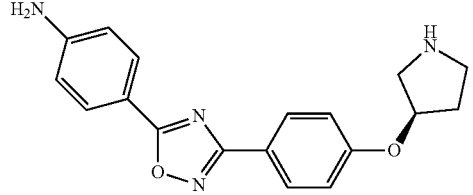
xvii
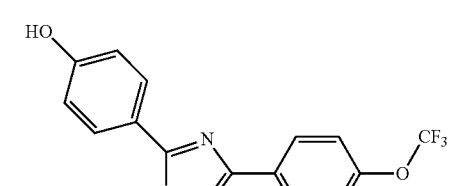
xviii
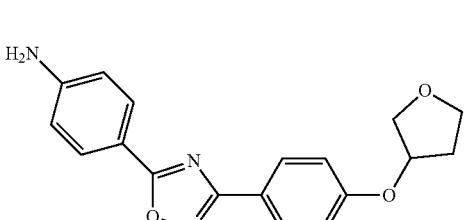
xix
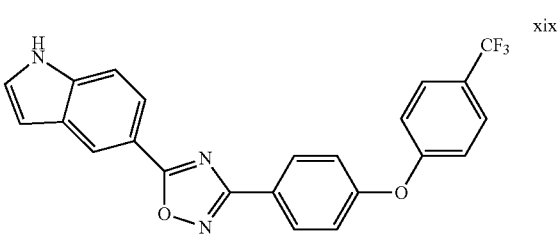
xx
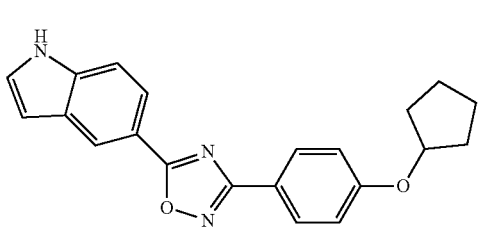
xxi
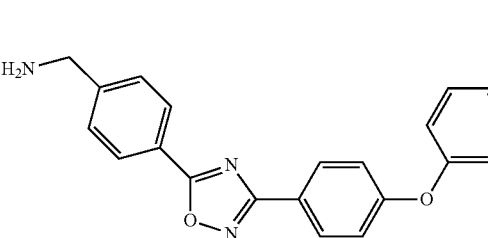
xxii
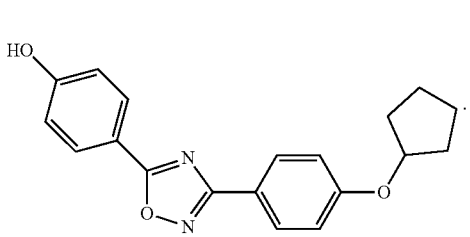

Embodiments of this disclosure include the use of a compound of Formula (A) for the therapeutic treatment of a *Clostridium difficile* bacterial infection, wherein Formula (A) is:

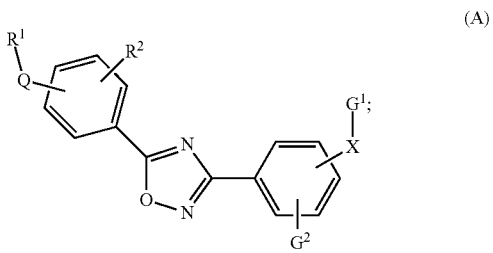

(A)

wherein

Q and X are each independently O, NH, N($C_1$-$C_4$(alkyl)), $CH_2$, or —(C=O)—;

$R^1$ and $G^1$ are each independently H, OH, $SO_2$($C_1$-$C_4$(alkyl)), aryl, heterocycle, ($C_1$-$C_8$)alkyl, or ($C_3$-$C_8$)cycloalkyl; and $R^2$ and $G^2$ are each independently H, OH, halogen, hydroxy, alkoxy, alkyl, amino, nitro, carboxyl, or —(C=O)$NH_2$, or $R^1$ is optionally bonded to $R^2$ to form a heterocycle;

wherein ($C_1$-$C_8$)alkyl and ($C_3$-$C_8$)cycloalkyl are saturated or optionally unsaturated, and wherein aryl, heterocycle, ($C_1$-$C_8$)alkyl and ($C_3$-$C_8$)cycloalkyl are optionally substituted with 1-3 substituents, wherein each substituent is independently halogen, oxo, hydroxy, alkoxy, $C_1$-$C_4$(alkyl), trifluoromethyl, trifluoromethoxy, or amino;

or a pharmaceutically acceptable salt or solvate thereof.

Various embodiments include the use of any one of the disclosed compounds, or a compound of the disclosed formulas, for the treatment of a *Clostridium difficile* bacterial infection. Other embodiments include the use of any one of the disclosed compounds for the treatment of *Clostridium difficile* bacterial infection comprising oral administration of the compound wherein less than 30 percent, 20 percent, 10 percent, or 5 percent of the compound is absorbed by the gastrointestinal tract. Several compounds were also evaluated for activity against *C. difficile* and were found to be equally or more effective toward *C. difficile* than *S. aureus*, as shown in the table below.

| Compound | *C. difficile* MIC |
|---|---|
| vii | 8 |
| ix | 2 |
| xi | 2 |
| xvii | 4 |
| xxi | 4 |
| xxii | 2 |

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound described or illustrated herein, which possess the useful properties described herein, it being well known in the art how to prepare optically active forms (for example, by synthesis from optically-active starting materials, by using resolution of the racemic form by recrystallization techniques, by chiral synthesis, or by chromatographic separation using a chiral stationary phase). Thus, the compounds of this invention include all stereochemical isomers arising from the various structural variations of these compounds.

Results and Discussion

Synthesis and Activity Profile of Oxadiazole 2

Oxadiazole 2 was synthesized in four steps as shown in Scheme 1. ND-421 and oxadiazole 2 was evaluated in 14 *C. difficile* strains, with vancomycin, metronidazole, and fidaxomycin as controls (Table 1). The minimally-inhibitory concentration (MIC) ranged from 1-2 µg/mL for ND-421 and oxadiazole 2, 0.25-1 µg/mL for vancomycin, 0.1-0.25 µg/mL for metronidazole, and ≤0.01-0.25 for fidaxomicin. The oxadiazoles had similar activity against NAP1/027 strains BAA-1870 and BAA-1803 as vancomycin.

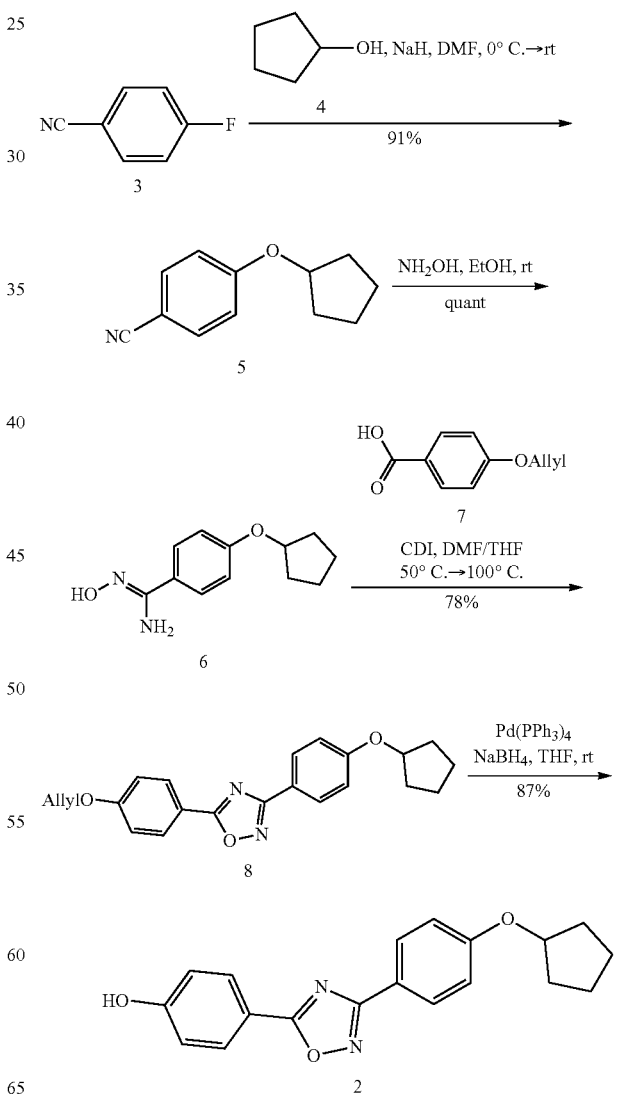

Scheme 1. Synthesis of oxadiazole 2.

TABLE 1

Minimal-inhibitory concentrations (MICs) of oxadiazoles (µg/mL) at 24 h and 48 h.

| | 1 | 2 | vancomycin | metronidazole | fidaxomicin |
|---|---|---|---|---|---|
| C. difficile ATCC43598[a] | 1/1 | 1/2 | 1/1 | 0.125/0.125 | 0.01/0.01 |
| C. difficile ATCC43255[b] | 2/2 | 2/2 | 0.5/0.5 | 0.01/0.01 | 0.01/0.01 |
| C. difficile BAA-1870[c] | 2/4 | 2/2 | 1/2 | 0.25/0.5 | <0.25/0.25 |
| C. difficile BAA-1804[d] | 2/2 | 2/2 | 1/1 | 0.25/0.25 | <0.25/<0.25 |
| C. difficile BAA-1803[e] | 1/2 | 1/2 | 1/2 | 0.25/0.5 | 0.5/1 |
| C. difficile BAA-1801[f] | 2/4 | 2/2 | 0.25/0.25 | 0.125/0.125 | 0.03/0.125 |
| C. difficile BAA-1812[g] | 2/2 | 2/2 | 0.25/0.5 | 0.25/0.25 | 0.015/0.125 |
| C. difficile BAA-1814[h] | 2/4 | 2/2 | 0.5/0.5 | 0.25/0.25 | ≤0.01/0.03 |
| C. difficile NR49310[i] | 2/2 | 2/4 | 0.25/0.5 | 0.125/0.125 | ≤0.01/≤0.01 |
| C. difficile NR49294[j] | 1/1 | 1/2 | 0.25/0.25 | 0.25/0.25 | ≤0.01/0.01 |
| C. difficile NR49305[k] | 2/4 | 2/2 | 0.25/0.5 | 0.25/0.25 | 0.01/0.01 |
| C. difficile NR49318[l] | 2/2 | 2/4 | 0.25/0.25 | 0.25/0.25 | 0.25/0.125 |
| C. difficile NR49292[m] | 1/2 | 1/2 | 0.25/0.25 | 0.125/0.25 | 0.25/0.5 |
| C. difficile NR49302[n] | 1/2 | 2/2 | 0.25/0.5 | 0.125/0.125 | 0.03/0.03 |

[a] isolated from human feces, toxinotype VIII, TcdA− (toxin A), TcdB+ (toxin B)
[b] isolated from abdominal wound, TcdA+, TcdB+
[c] NAP1, BI 8, ribotype 27, toxinotype IIIb, TcdA+, TcdB+, CDT+ (binary toxin)
[d] toxinotype 0, ribotype 053 TcdA+, TcdB+, CDT+
[e] clinical isolate, NAP1, toxinotype IIIc, ribotype 027, tcdA+, tcdB+, cdtB+
[f] isolated from human feces, nontoxigenic, TcdA−, TcdB−, ribotype 010
[g] toxinotype XII, ribotype 024, TcdA+, TcdB+, CDT−
[h] toxinotype XXII, ribotype 251, TcdA+, TcdB−, CDT+
[i] isolated from human feces, NAP7, ribotype 078, TcdA+, TcdB+, TcdC+, (Δ39), CDT+
[j] isolated from human feces, NAP4, ribotype 014, TcdA+, TcdB+, TcdC+, CDT−, most prevalent after NAP1/027
[k] isolated from human feces, NAP6, ribotype 002, TcdA+, TcdB+, TcdC+, CDT−, community associated epidemic strain
[l] isolated from human feces, NAP11, ribotype 106, TcdA+, TcdB+, TcdC+, CDT−, predominant epidemic strain in a children's hospital in Chicago, increased risk of relapses
[m] isolated from human feces, NAP2, ribotype 001_072, TcdA+, TcdB+, TcdC+, CDT−, epidemic in US during 1990s and still common
[n] isolated from human feces, NAP4, ribotype 020, TcdA+, TcdB+, TcdC+, CDT−, among top 7 isolates in 2011-2012

The activity of oxadiazoles 1 and 2 against common gut bacteria was investigated. The oxadiazoles were not active against *Lactobacillus reuteri*, *Lactobacillus gasseri*, and *Veillonella* sp. (Table 2).

TABLE 2

Minimal-inhibitory concentrations (MICs) of oxadiazoles (µg/mL) against common gut bacteria.

| | 1 | 2 | vancomycin | metronidazole | fidaxomicin |
|---|---|---|---|---|---|
| Bacteroides fragilis HM-709[a] | 2 | 1 | 16 | 0.5 | >32 |
| Bacteroides fragilis | 4 | 2 | 16 | 1 | >32 |
| Bacteroides ovatus | 4 | 2 | 16 | 2 | >32 |
| Bacteroides vulgatus | 2 | 2 | 16 | 2 | >32 |
| Bacteroides eggerthii | 2 | 1 | 8 | 2 | >32 |
| Bacteroides caccae | 4 | 2 | 32 | 2 | >32 |
| Bifidobacterium longum HM-846[b] | 0.2 | 1 | 0.25 | 0.5 | <0.01 |
| Corynebacterium sp. HM-784[c] | 2 | 0.5 | 0.25 | >32 | <0.06 |
| Fusobacterium nucleatum HM-992[d] | 1 | 2 | 0.25 | 2 | <0.06 |
| Lactobacillus reuteri HM-102[e] | >12 | >128 | >32 | >32 | >32 |
| Lactobacillus gasseri HM-644[f] | >12 | >128 | 1 | >32 | 2 |
| Veillonella sp. HM-49[g] | >12 | >128 | >32 | 2 | 8 |
| Eubacterium sp. HM-178[h] | 2 | 4 | 2 | 1 | 16 |

Figure 1B:
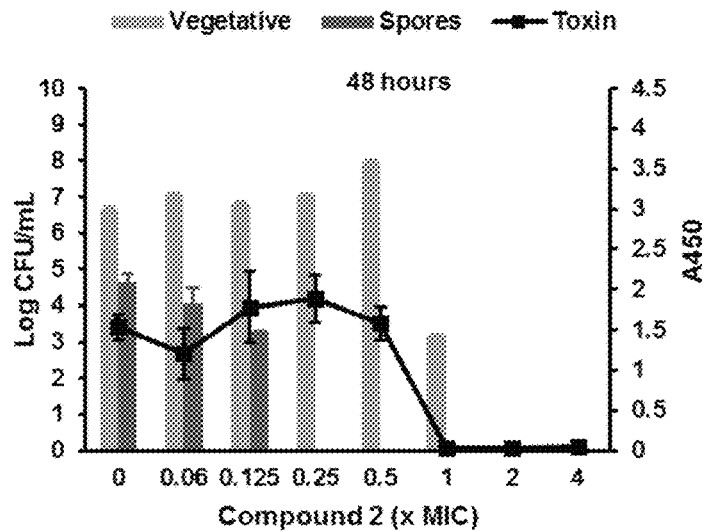
Figure 1C:
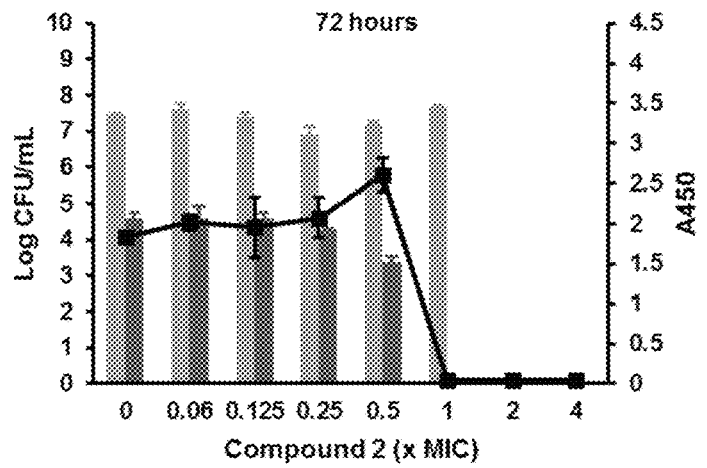

[a] Gram-negative, anaerobic bacterium that is commensal and critical to host immunity; a minor component of the human gut microflora (<1%)
[b] Anaerobic, Gram-positive bacterium commonly found in the normal human intestinal microflora
[c] Isolated from human feces, non-sporulating, Gram-positive, aerobic or facultatively anaerobic bacterium that occurs in the mucosa and normal skin flora of humans and animals
[d] Anaerobic, non-sporulating, Gram-negative bacterium commonly found in the gastrointestinal tract
[e] Gram-positive, anaerobic bacteria commonly found in the normal human gastrointestinal tract, commonly used as a probiotic to maintain balance of gut microbial flora
[f] Gram-positive, facultative, anaerobe bacterium commonly found in the normal human gastrointestinal tract, commonly use in yougurt production as a probiotic to suppress *Helicobacter pylori* infections
[g] Gram-negative, non-sporulating bacterium commonly found in the intestinal tract of humans and animals
[h] Anaerobic, non-sporulating, Gram-positive bacterium commonly found in the gastrointestinal flora of humans and animals Oxadiazole 2 Inhibits Vegetative Cells, Spores, and Toxin Production We evaluated compound 2 for its ability to inhibit *C. difficile* vegetative cells, spores, and toxin production. At 24 hours, oxadiazole 2 inhibited growth of vegetative cells, as well as toxin production at 1× MIC (FIG. 1); there were no spores produced. At 48 hours, oxadiazole inhibited spore production at ¼ MIC and toxin production at 1× MIC; at 72 hours, vegetative cells, spores, and toxin production were inhibited at 1× MIC.

Oxadiazole 2 is Poorly Absorbed

Figures 2A, 2B:
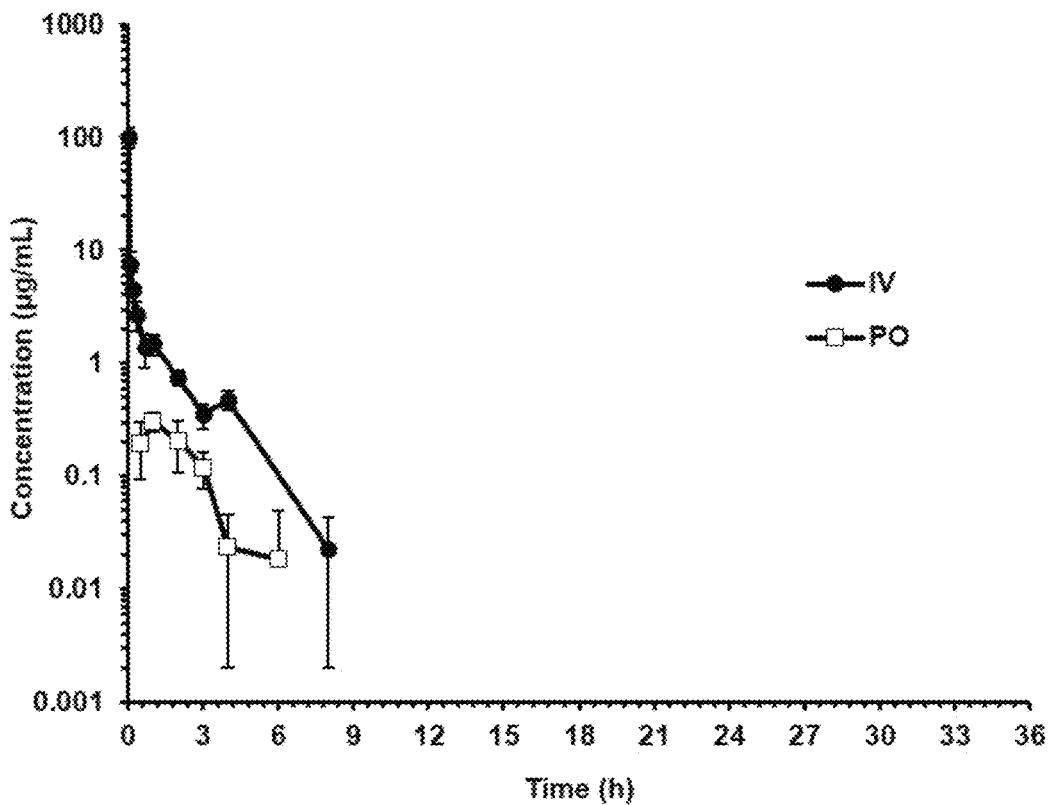
FIG. 2A-2B. Plasma concentration-time curves after a single po and iv administration of oxadiazole 2 at 20 mg/kg to mice (n=3 per time point per route of administration) (A). Comparison of area-under-the-curves give absolute oral bioavailability F of 3.8% for oxadiazole 2 (B).

The pharmacokinetics of oxadiazole 2 were investigated after single oral (po) and intravenous (iv) administration to uninfected mice. Concentrations versus time are shown in FIG. 2A and pharmacokinetic parameters are summarized in FIG. 2B. After a 20 mg/kg iv dose of oxadiazole 2, clearance was moderate at 17.4 mL/min/kg (approximately 20% of hepatic blood flow), the volume of distribution ($V_d$) of 1.8 L/kg was large indicating that the compound distributed to tissues, and the elimination half-life was 1.2 h. Systemic exposure as measured by the area-under-the-curve ($AUC_{0-\infty}$) was 1149 μg·min/mL after iv administration and 44 μg·min/mL following a po dose, giving an absolute oral bioavailability of 4%. $C_{max}$ of 0.30 μg/mL was attained at 1 h and the elimination half-life was 1.1 h. Feces were collected from the mice via metabolism cages and levels of oxadiazole 2 were 43±3 μg/g (equivalent to 43±3 μg/mL assuming a density of 1 g/mL) or about 20× MIC at 24 h after a single 20 mg/kg po dose. For in vivo efficacy against *C. difficile*, antibiotics with poor oral bioavailability that are poorly absorbed (or not absorbed) are needed for treatment of this difficult pathogen in the gastrointestinal tract. Oxadiazole 2 and related oxadiazoles described herein fit these criteria.

Oral Administration of Oxadiazole 2 Results in High Concentrations in the Gut and Is Well Tolerated in Mice We evaluated the toxicity of oxadiazole 2 in uninfected mice after multiple-dose oral administration at 40 mg/kg/day for 5 days. We also collected feces and analyzed them by ultraperformance liquid chromatography (UPLC) with multiple-reaction monitoring (MRM) detection. Oxadiazole 2 was well tolerated and did not result in weight loss (Table 3). On day 5, concentrations of oxadiazole 2 were 30.8±11.1 μg/g (equivalent to 30.8 μg/mL assuming a density of 1 g/mL, Table 3), 15- to 30-fold higher than MIC.

TABLE 3

Concentration of oxadiazole 2 in feces after multiple oral dose administration.

| Day | Oxadiazole 2 in Feces (μg/g feces) | Body weight (g) |
| --- | --- | --- |
| 1 | 9.8 ± 0.4 | 19.6 ± 0.6 |
| 2 | 15.0 ± 3.7 | 19.8 ± 0.6 |
| 3 | 18.1 ± 2.4 | 19.8 ± 1.0 |
| 4 | 16.9 ± 1.8 | 19.7 ± 1.0 |
| 5 | 30.8 ± 11.1 | 19.4 ± 0.6 |

Oxadiazole 2 Inhibits Cell Wall Synthesis

Figure 3:
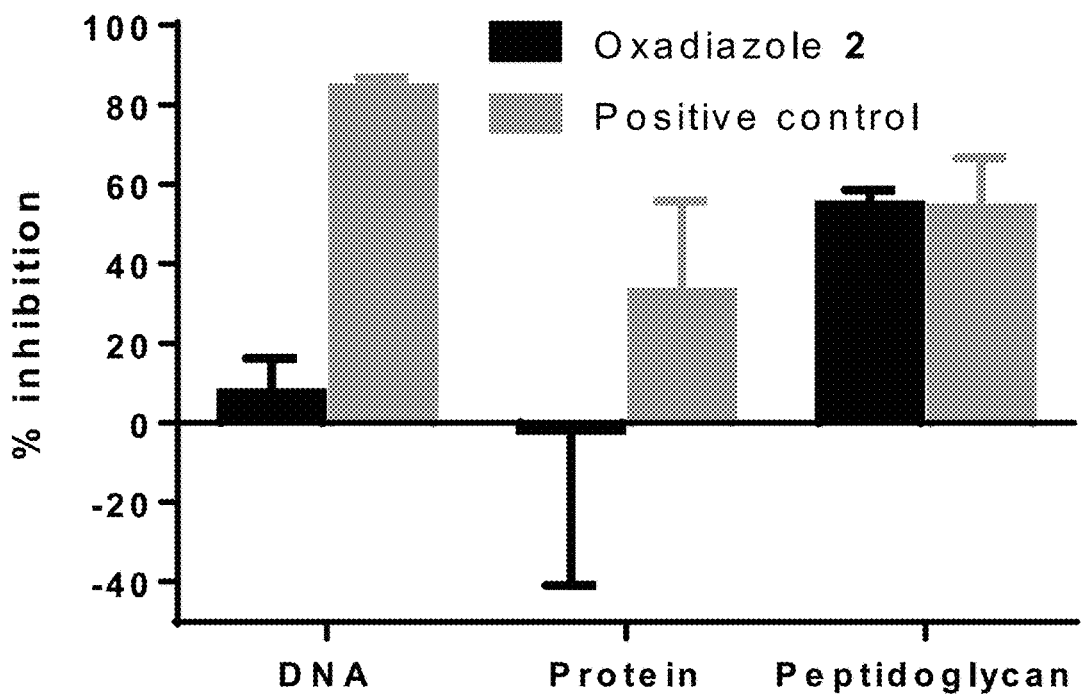
FIG. 3. Oxadiazole 2 inhibits peptidoglycan synthesis in *C. difficile* by macromolecular synthesis assays. Oxadiazole 2 was incubated at ½, 1, or 2× MIC; data shown are for ½ MIC; positive controls were ciprofloxacin (MIC 8 μg/mL) for DNA, linezolid (MIC 2 μg/mL) for protein, and oxacillin (MIC 8 μg/mL) for peptidoglycan. Maximum inhibition for oxadiazole 2 was observed at 60 min incubation for DNA, at 180 min for protein, and at 120 min for peptidoglycan.
Figure 4:
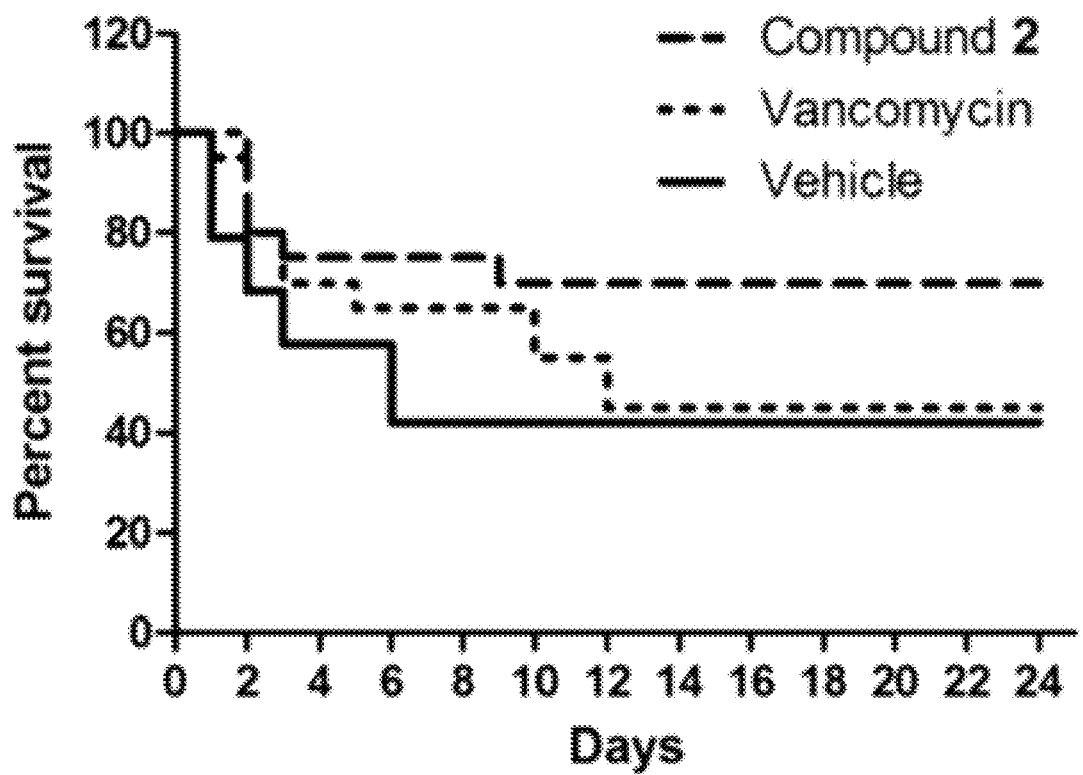
FIG. 4. Oxadiazole 2 is efficacious in a mouse model of recurrent CDI. Mice (n=10 per group) were given antibiotic cocktail (0.4 mg/mL kanamycin, 0.035 mg/mL gentamicin, 850 U/mL colistin, 0.215 mg/mL metronidazole, and 0.045 mg/mL vancomycin added to the drinking water for five days. After two days, mice were administered a single 10 mg/kg intraperitoneal dose of clindamycin. One day later, the mice were infected with $10^5$ cfu of *C. difficile* strain ATCC 43255 intragastrically. Oxadiazole 2 was given po at 20 mg/kg/day starting one hour after infection once a day for 5 days; vancomycin was administered po at 50 mg/kg/day for 5 days. Survival was monitored for 25 days post-infection. Results are the average of two separate studies.

We investigated the mechanism of action of oxadiazole 2 using the macromolecular synthesis assay with *C. difficile* ATCC 43255. Incorporation of radiolabeled [2,8-³H]adenine into DNA, 1-[3,4,5-³H(N)]-leucine into protein, and N-acetyl-d-[6-³H]-glucosamine into peptidoglycan (cell wall) was monitored and compared to positive controls (ciprofloxacin, linezolid, and oxacillin for DNA, protein, and peptidoglycan, respectively). Oxadiazole 2 inhibited peptidoglycan synthesis 54.8±3.7% compared to 54.1±13 for the positive control oxacillin (FIG. 3). In contrast, inhibition of DNA or protein by oxadiazole 2 was not significant.

Efficacy of Oxadiazole 2 in a Mouse Model of Recurrent CDI

We next evaluated oxadiazole 2 in the mouse model of recurrent CDI developed by Chen et al. (*Gastroenterology* 2008, 135(6), 1984). While several animal models are available to study CDI, the most widely used animal model of CDI is the hamster, as the hamster is readily susceptible to CDI. However, in hamsters primarily the cecum and ileum are affected and animals develop severe enterocolitis and quickly die. As such, the hamster model does not reproduce the typical course of disease in humans. The mouse model parallels the human disease in that the entire colon is affected. The model results in variable disease severity, which resurges after vancomycin therapy, and is a recurrent disease in animals that survive the initial infection. Mice were treated with a mixture of kanamycin, gentamicin, colistin (850 U/mL), metronidazole, and vancomycin in the drinking water for five days, and clindamycin given intraperitoneally two days later. The following day mice were infected with *C. difficile* strain ATCC 43255 intragastrically. Oxadiazole 2 was given po at 20 mg/kg/day starting one hour after infection once a day for 5 days; vancomycin was administered po at 50 mg/kg/day for 5 days. After 25 days, survival was 45% in vancomycin, 70% in oxadiazole 2, and 40% in vehicle (FIG. 3). Fecal pellets or diarrhea smears were collected from the surviving mice and plated for vegetative cell and spore counts, as well as analyzed for TcdA and TcdB toxins by ELISA. Compound 2 resulted in about 3-log reduction in vegetative cells by day 10, 3-log decrease in spores were observed in the 20 mg/kg group, while the 40 mg/kg group showed no spores on days 3, 7, and 10 (FIG. 3B). In contrast, vancomycin resulted in 2-log reduction in vegetative cells; no spores were observed until day 10.

Figure 5A:
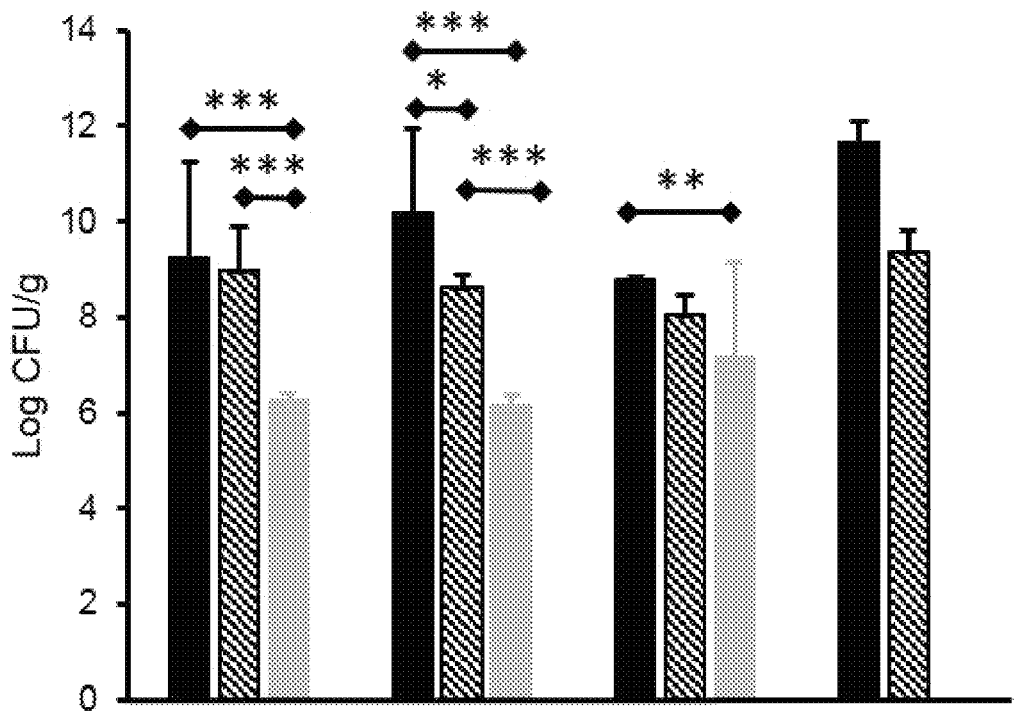
FIG. 5A-5B. Oxadiazole 2 reduces *C. difficile* cell count and spores in feces. (A) total cell count and (B) spore count after ethanol treatment of fecal samples. Day 3: n=7 mice in 20 mg/kg oxadiazole 2, 3 mice in 40 mg/kg oxadiazole 2, 7 mice in vancomycin, and 5 in vehicle; Day 7: n=8 in 20 mg/kg oxadiazole 2, 6 in 40 mg/kg oxadiazole 2, 4 animals in vancomycin group, and 4 in vehicle; Day 10: n=8 in 20 mg/kg oxadiazole 2, 7 in 40 mg/kg oxadiazole 2, 5 in vancomycin; no samples obtained in vehicle group on day 10.
Figure 5B:
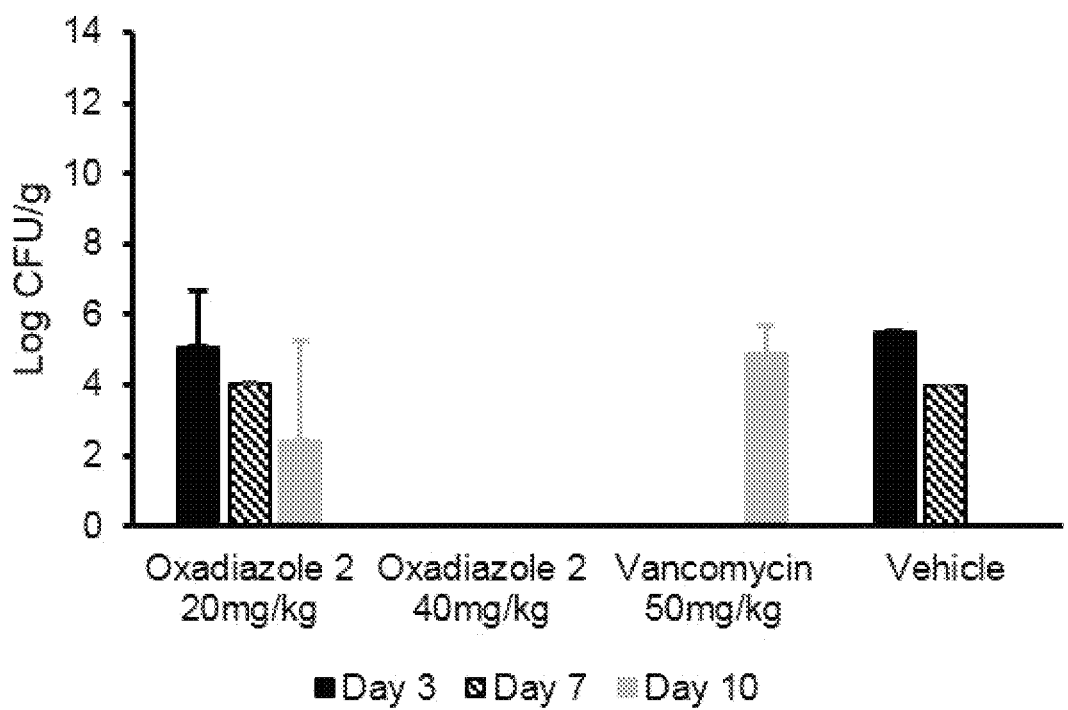

Subsequently, colony counts in feces were conducted following treatment with oxadizole 2 at 20 or 40 mg/kg/day for 5 days. Total cell counts were 3.44 log lower on day 10 in the 20 mg/kg oxadiazole 2 group and 4.68 log lower in the 40 mg/kg group compared to day 3, while the vancomycin-treated group showed 1.02 log reduction (FIG. 5A). Treatment with 20 mg/kg oxadiazole 2 resulted in 1.85 log reduction in spores, while no spores were observed at any time in mice given 40 mg/kg oxadiazole 2 (FIG. 5B). Mice treated with 50 mg/kg vancomycin did not produce spores initially, however once vancomycin treatment stopped spores were observed on day 10 (FIG. 5B). The vancomycin results are consistent with those observed by Chen et al. due to recurrence/relapsing CDI after discontinuation of treatment with vancomycin. Likewise, no toxin production was detected in the 40 mg/kg oxadiazole 2 group, while toxin was observed in the vancomycin group on day 10 (Table 4). These studies demonstrate that oxadiazole 2 has in vivo efficacy in a mouse model of recurrent CDI.

TABLE 4

TcdA and TcdB toxin detection in *C. difficile* infected mice.

|  | Day 3 | Day 7 | Day 10 |
| --- | --- | --- | --- |
| Compound 2 (20 mg/kg) | + | + | + |
| Compound 2 (40 mg/kg) | − | − | − |

TABLE 4-continued

TcdA and TcdB toxin detection in *C. difficile* infected mice.

|  | Day 3 | Day 7 | Day 10 |
|---|---|---|---|
| Vancomycin (50 mg/kg) | − | − | + |
| Vehicle | + | + | |

General Synthetic Methods

In general, preparation of the compounds and formulas described herein, and modifications thereof, can be made according to organic synthesis techniques known to those of skill in the art and/or according to the synthetic schemes provided herein, such as Scheme 1 above. Where desired, synthesis of a subject compound can begin with commercially available chemicals, from compounds described in the chemical literature, or from products of the reactions and methods described herein. Commercially available compounds may be obtained from standard commercial sources including Acros Organics (Pittsburgh, Pa.), Aldrich Chemical (Milwaukee, Wis., including Sigma Chemical and Fluka), Eastman Organic Chemicals, Eastman Kodak Company (Rochester, N.Y.), Fisher Scientific Co. (Pittsburgh, Pa.), ICN Biomedicals, Inc. (Costa Mesa, Calif.), Lancaster Synthesis (Windham, N.H.), Spectrum Quality Product, Inc. (New Brunswick, N.J.), TCI America (Portland, Oreg.), Combi-Blocks, Inc. (San Diego, Calif.), Oakwood Products, Inc. (Estill, S.C.), and Wako Chemicals USA, Inc. (Richmond, Va.).

In addition, methods known to one of ordinary skill in the art may be identified through various reference books and databases. Suitable reference books and treatises that detail the synthesis of reactants useful in the preparation of the inhibiting agents described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992; and *Protecting Groups in Organic Synthesis, Second Edition*, Greene, T. W., and Wutz, P. G. M., John Wiley & Sons, New York.

Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Unless specified to the contrary, the reactions described herein take place at atmospheric pressure, generally within a temperature range from −10° C. to 200° C. Further, except as otherwise specified, reaction times and conditions are intended to be approximate, e.g., taking place at about atmospheric pressure within a temperature range of about −10° C. to about 110° C. over a period of about 1 to about 24 hours; reactions left to run overnight average a period of about 16 hours.

A number of exemplary methods for preparation of the compounds of the invention are provided below. These methods are intended to illustrate the nature of such preparations are not intended to limit the scope of applicable methods. Other variations, such as adding various substituents (e.g., as defined above) on various alkyl, cycloalkyl, aryl, or heterocycle groups are included in the scope of the invention. Relevant starting materials can typically be purchased from the commercial suppliers cited above (e.g., from Sigma-Aldrich, Milwaukee, Wis.) or they can be prepared in a few standard steps from commercially available materials.

In various embodiments, compounds of the formulas described herein can be prepared by the following representative methods, as illustrated by Schemes 2-8.

Scheme 2. General oxadiazole synthesis.

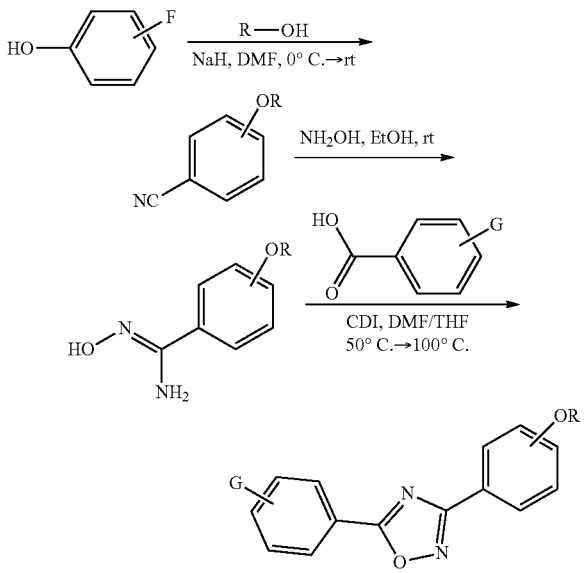

where R and G are substituent groups as defined above, and for example, and recited for $R^1$ and $G^1$ in Formulas I and A. As indicated above, R (i.e., —OR) and G can be located at any available position on their respective phenyl rings, ortho, meta, or para to the site of attachment to the oxadiazole moiety. Furthermore, R or G can be an ortho-fused heterocycle or heteroaryl group, as represented by the respective moiety in one or more of compounds i-xxii. In other embodiments, the oxygen atom of —OR can be replaced with a nitrogen to provide a —NH—R substituent (see Scheme 5). Additional examples of compounds of the invention and methods for their preparation are provided in the schemes below.

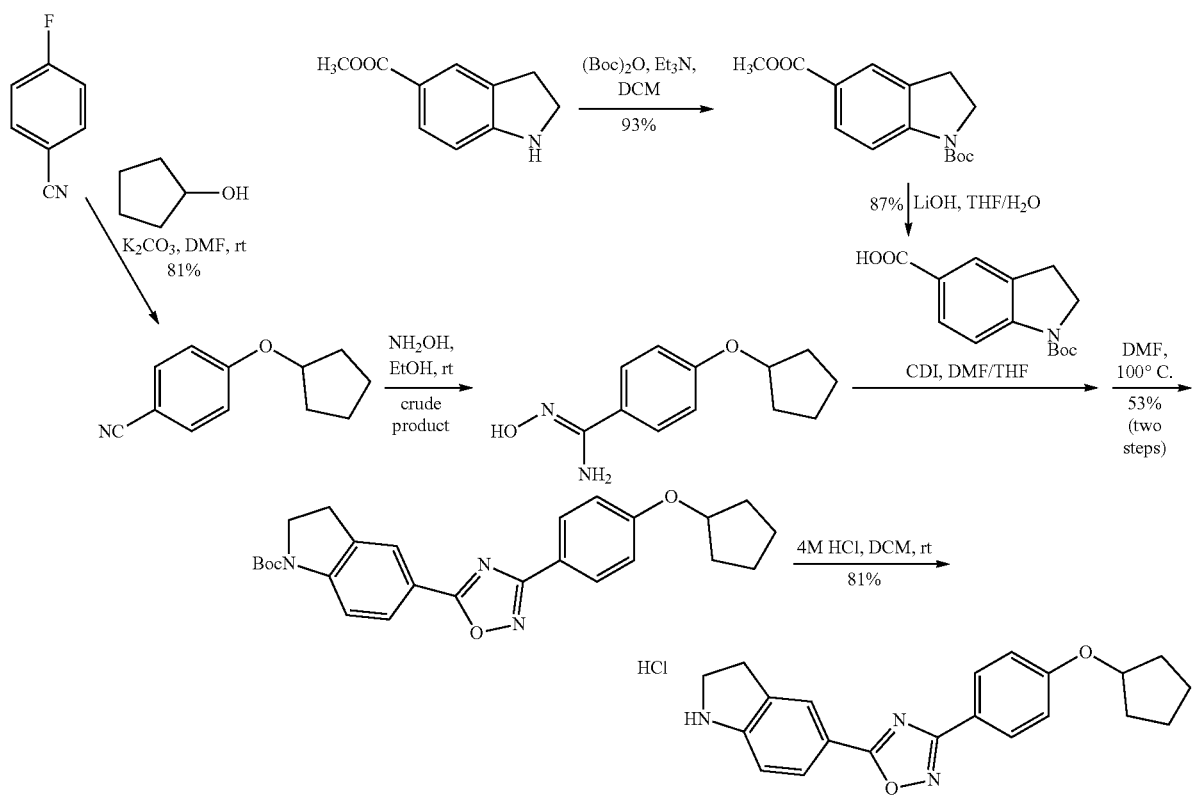
Scheme 3.
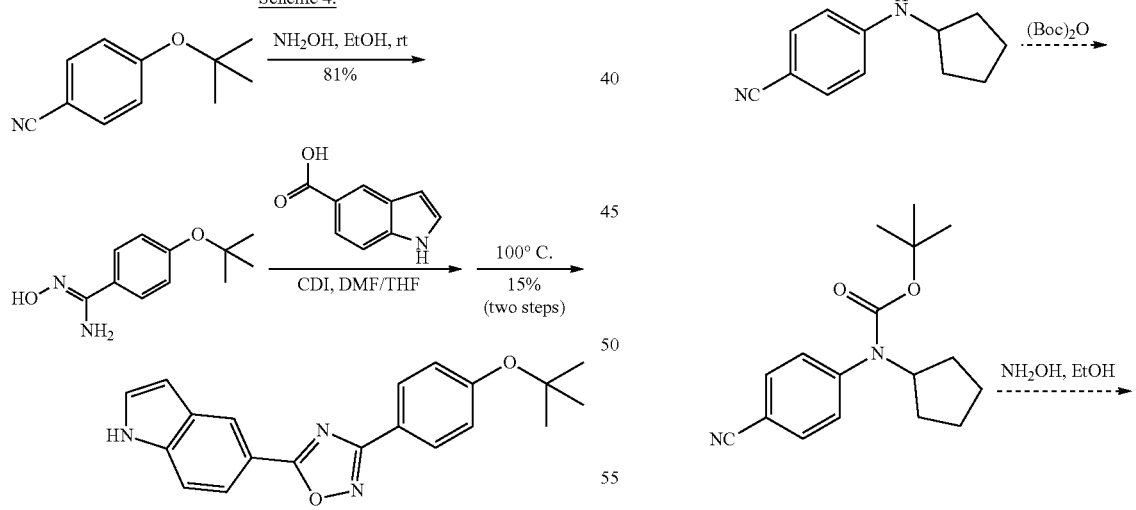
Scheme 4.
Scheme 5.

-continued
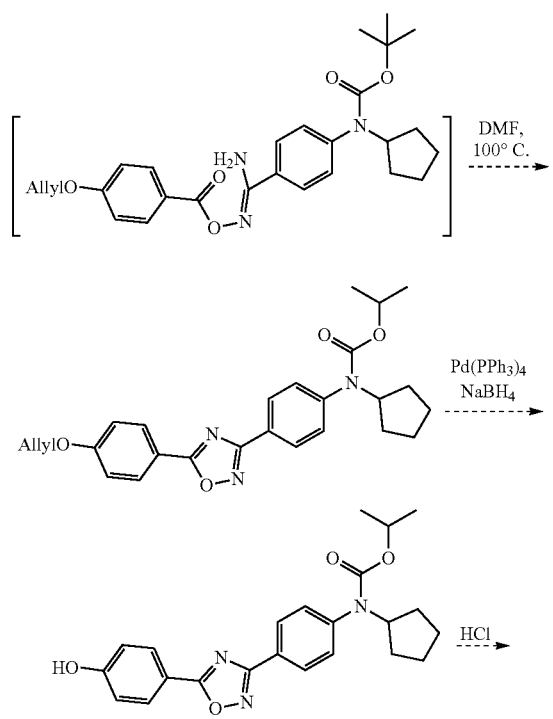
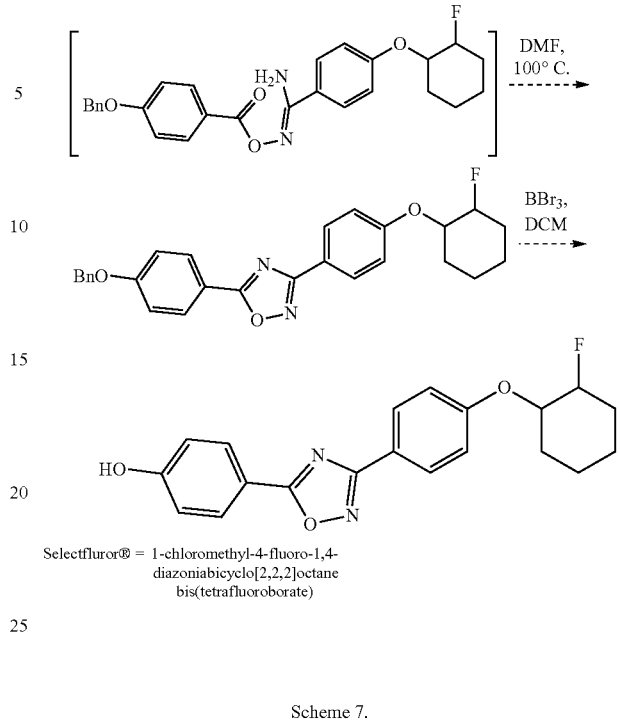
Selectfluror® = 1-chloromethyl-4-fluoro-1,4-diazoniabicyclo[2,2,2]octane bis(tetrafluoroborate)
Scheme 6.
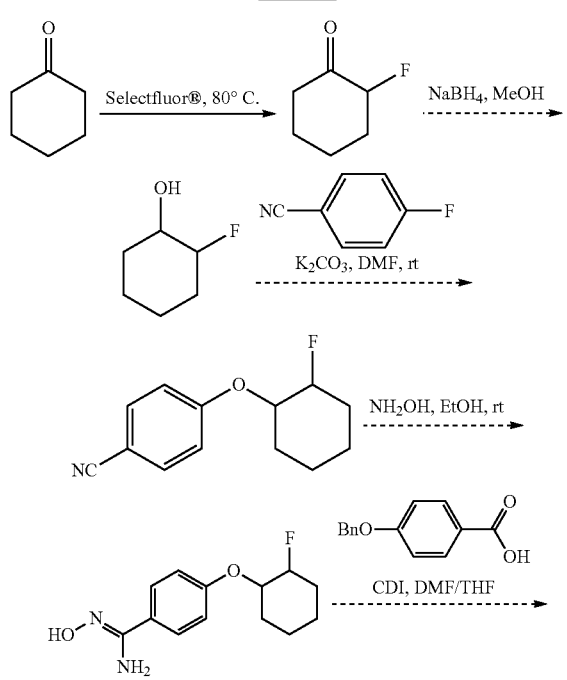
Scheme 7.
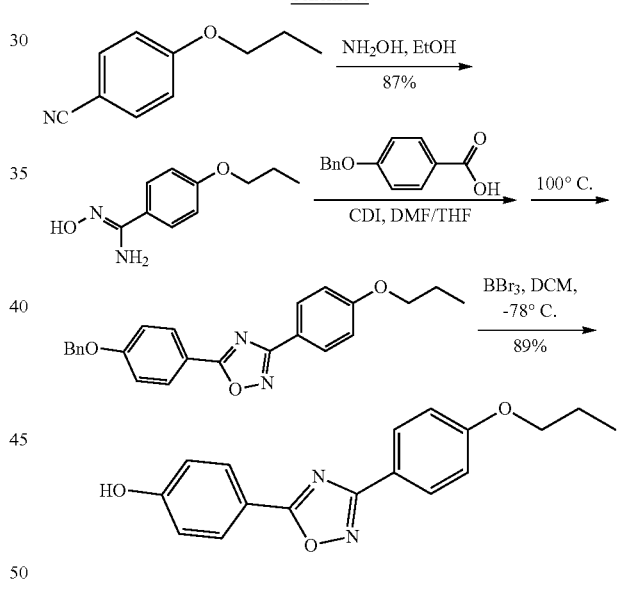
Scheme 8.
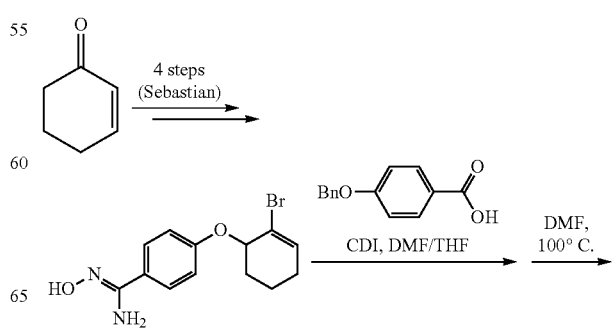

-continued

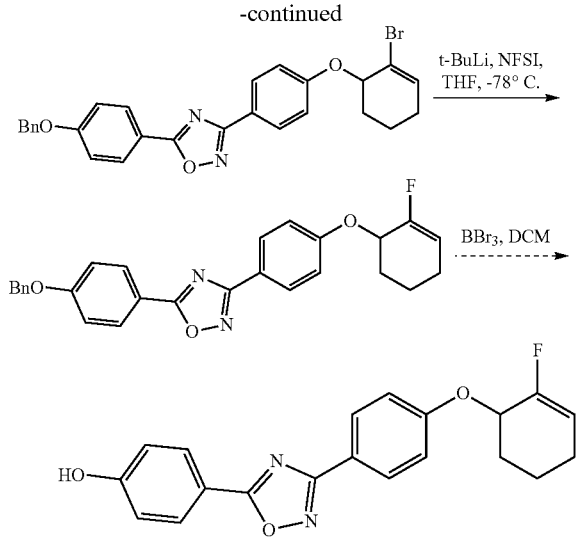

NFSI = N-fluorobenzenesulfonimide

As would be readily recognized by one of skill in the art, various other substituents (e.g., $R^1$ and $G^1$ groups of Formulas A and I) can be installed by selection of the appropriate commercially available starting material and/or the relevant starting material can be prepared by standard synthetic techniques known to those of skill in the art to provide the compounds of the formulas described herein.

Pharmaceutical Formulations

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiologically acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of enteral administration, e.g., oral administration, sublingual administration, or rectal administration.

The compounds described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms include aqueous solutions, dispersions, or sterile powders comprising the active ingredient, optionally encapsulated in liposomes. The ultimate dosage form should be sterile, fluid and stable under the conditions of manufacture and storage. A liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the compositions can be brought about by agents capable of delaying absorption, for example, aluminum monostearate and/or gelatin.

Various dosage forms can be prepared by incorporating the active compound in the required amount in the appropriate solvent with various other ingredients enumerated above, optionally followed by filter sterilization. Methods of preparation can include vacuum drying and freeze-drying techniques, which yield a powder of the active ingredient plus any additional desired ingredient present in the solution.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be administered orally or sprayed into the mouth using a pump-type or aerosol sprayer. Thickeners such as synthetic polymers, fatty acids, fatty acid salts and esters, fatty alcohols, modified celluloses, or modified mineral materials can also be employed with liquid carriers.

Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The compound can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The compounds described herein can be effective antibacterial agents and have higher potency and/or reduced toxicity as compared to vancomycin. Preferably, compounds of the invention are more potent and less toxic than vancomycin, and/or avoid a potential site of catabolic metabolism encountered with vancomycin, and have a different pharmacokinetic profile than vancomycin.

The invention provides therapeutic methods of treating bacterial infections in a mammal, which involve administering to a mammal having bacterial infection an effective amount of a compound or composition described herein. A mammal includes a primate, human, rodent, canine, feline, bovine, ovine, equine, swine, caprine, bovine and the like. Bacterial infections refer to any various type of bacterium that causes debilitating or life-threatening health issues.

The ability of a compound of the invention to treat bacterial infections may be determined by using assays well known to the art. For example, the design of treatment protocols, toxicity evaluation, data analysis, quantification of bacterial cell death, and the biological significance of the use of bacterial screens are known. In addition, ability of a compound to treat bacterial infections may be determined using the protocols as described herein.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

Materials and Methods

Abbreviations. AUC, area under the curve; CDI, *C. difficile* infection; DMF, dimethylformamide; DMSO, dimethyl sulfoxide; ESI, electrospray ionization; HRMS, high resolution mass spectrometry; ip, intraperitoneal; iv, intravenous; MIC, minimally-inhibitory concentration, MRM, multiple reaction monitoring; MS, mass spectrometry; PK, pharmacokinetic; po, oral; THF, tetrahydrofuran; TLC, thin-layer chromatography; UPLC, ultra-performance liquid chromatography.

Synthesis. All chemicals, reagents, and solvents were used directly as purchased without further purification. Analytical thin-layer chromatography was performed on silica gel 60 F$_{254}$. For column chromatography, silica gel 60, 230-400 mesh, 40-63 μm was used. $^1$H NMR and $^{13}$C NMR spectra were recorded on Bruker AVANCE III HD 500 spectrometers (Bruker Daltonik, Bremen, Germany) and operated at an $^1$H resonance frequency of 500.13 MHz. Chemical shifts are referenced to the residual deuterated solvent (e.g., for CDCl$_3$, δ=7.26 and 77.16 ppm for $^1$H and $^{13}$C NMR, respectively) and reported in parts per million (ppm, δ) relative to tetramethylsilane (TMS, δ=0.00 ppm). Coupling constants (J) are reported in Hz, where s=singlet, d=doublet, t, triplet, m=multiplet, br=broad. High-resolution mass spectra were measured using a Bruker micrOTOF/Q2 mass spectrometer in electron spray ionization source (ESI) ionization.

4-(Cyclopentyloxy)benzonitrile (5)

Cyclopentanol (4) (1.54 g, 18 mmol) and 0.72 g NaH were placed at 50 mL two-neck reaction flask at 0° C. 4-Fluorobenzenitrile (3) (1.81 g, 15 mmol) in 3 mL DMF was added to the above mixture. The reaction mixture was stirred at 0° C. for 15 minutes and was allowed to come to room temperature. The reaction was monitored by TLC and was complete after 2 h. The mixture was quenched in iced water and extracted with ethyl acetate (3×50 mL). The organic phases were combined and dried over anhydrous Na$_2$SO$_4$, followed by filtration and concentration of the filtrate under reduced pressure. The residue was purified on silica gel chromatography (hexane/ethyl acetate, 25:1) to give compound 5 as a colorless oil (3.06 g, 91%).

$^1$H NMR (500 MHz, CDCl$_3$) δ 1.65–1.59 (m, 2H), 1.83–1.75 (m, 4H), 1.94–1.90 (m, 2H), 4.77 (t, J=2.5 Hz, 1H), 6.89–6.86 (m, 2H), 7.53–7.50 (m, 2H). $^{13}$C NMR (125 MHz, CDCl$_3$) δ 24.2, 32.9, 80.1, 103.3, 116.2, 119.6, 134.0, 161.7; HRMS [M+H]$^+$, calcd for C$_{12}$H$_{14}$NO 188.1070; found 188.1099.

(Z)-4-(Cyclopentyloxy)-N'-hydroxybenzimidamide (6)

Compound 5 (4.47 g, 23.89 mmol) was dissolved in ethanol (125 mL) in a 200-mL reaction flask. NH$_2$OH (50%, 5.6 mL) was added and the mixture was stirred at room temperature for 50 h until the reaction was complete as monitored by TLC. The solvent was evaporated under reduced pressure to afford the product as a white solid (5.26 g, 100%).

$^1$H NMR (500 MHz, DMSO-d$_6$) δ 1.58–1.52 (m, 2H), 1.70–1.63 (m, 4H), 1.92–1.82 (m, 2H), 4.81–4.78 (m, 1H), 5.70 (s, 2H), 6.87–6.84 (m, 2H), 7.58–7.55 (m, 2H). $^{13}$C NMR (125 MHz, DMSO-d$_6$) δ 24.3, 32.9, 79.3, 115.5, 126.0, 127.4, 151.3, 158.9; HRMS [M+H]$^+$, calcd for C$_{12}$H$_{17}$N$_2$O$_2$ 221.1824; found 211.1283.

5-(4-(Allyloxy)phenyl)-3-(4-(cyclopentyloxy)phenyl)-1,2,4-oxadiazole (8)

Compound 6 (0.62 g, 3.5 mmol) and 1,1'-carbonyldiimidazole (0.53 g, 3.25 mmol) were dissolved in 4 mL DMF at 50° C. The mixture was stirred for 15 minutes and compound 7 (0.55 g, 2.5 mmol) in 15 mL THF was added. The temperature was increased to 100° C. and the reaction was complete after 14 h. The reaction was quenched with saturated NH$_4$Cl solution and was extracted with ethyl acetate (25 mL, 3×). The organic phases were combined, dried over anhydrous Na$_2$SO$_4$, filtered, and concentrated under reduced pressure. The crude material was purified on silica gel chromatography (hexane/ethyl acetate, 50:1) to give the title compound 8 as a viscous oil (0.70 g, 78%).

$^1$H NMR (500 MHz, CDCl$_3$) δ 1.66–1.60 (m, 2H), 1.97–1.75 (m, 6H), 4.62–4.61 (m, 2H), 4.84–4.82 (m, 1H), 5.34–5.32 (m, 1H), 5.46–5.42 (m, 1H), 6.09–6.02 (m, 1H), 6.96 (d, J=9.0 Hz, 2H), 7.03 (d, J=9.0 Hz, 2H), 8.06 (d, J=9.0 Hz, 2H), 8.13 (d, J=9.0 Hz, 2H). $^{13}$C NMR (125 MHz, CDCl$_3$) δ 24.3, 33.1, 69.2, 79.7, 115.4, 115.9, 117.4, 118.4, 119.3, 129.2, 130.2, 132.7, 160.7, 162.3, 168.8, 175.4; HRMS [M+H]$^+$, calcd for C$_{22}$H$_{23}$N$_2$O$_3$ 363.1703; found 363.1709.

4-(3-(4-(Cyclopentyloxy)phenyl)-1,2,4-oxadiazol-5-yl)phenol (2)

A 50-mL flask was charged with Pd(PPh$_3$)$_4$ (19 mg, 0.016 mmol) and compound 6 (0.30 g, 0.82 mmol) in 12 mL THF under Ar atmosphere at room temperature. The mixture was stirred for 5 minutes and NaBH$_4$ (47 mg, 1.23 mmol) was added. The reaction mixture was stirred for 1.5 h, quenched with aqueous HCl (1M, 3 mL), and extracted with ethyl acetate (3×20 mL). The organic phases were combined and dried over anhydrous Na$_2$SO$_4$, followed by filtration and concentration under reduced pressure. The residue was purified on silica gel chromatography (hexane/ethyl acetate, 6:1) to afford 2 as white solid (0.23 g, 87%).

$^1$H NMR (500 MHz, DMSO-d$_6$) δ 1.61–1.55 (m, 2H), 1.74–1.66 (m, 4H), 1.98–1.90 (m, 2H), 4.91–4.83 (m, 1H), 6.99–6.96 (m, 2H), 7.07–7.04 (m, 2H), 8.00–7.94 (m, 4H); $^{13}$C NMR (125 MHz, DMSO-d$_6$) δ 24.3, 32.9, 79.7, 114.9, 116.5, 116.9, 118.9, 129.4, 130.7, 160.8, 162.6, 168.4, 175.8; HRMS [M+H]$^+$, calcd for C$_{19}$H$_{19}$N$_2$O$_3$ 323.1390; found 323.1419.

Antibiotics. Vancomycin and metronidazole were purchased from Sigma Aldrich (St. Louis, Mo.) and fidaxomicin was obtained from BOC Sciences (Shirley, N.Y.).

Bacterial strains. The strains used in the study were obtained from ATCC (Manassas, Va.) and BEI Resources (Manassas, Va.). All the strains were cultured and stored according to the supplier instructions.

Minimally-inhibitory concentrations. MICS for *C. difficile* strains and the common gut bacteria were determined using broth microdilution techniques as reported earlier using brucella broth supplemented with hemin and vitamin K or supplemented BHIS broth (Babakhani et al., *J Antimicrob Chemother* 2013, 68(3), 515). *Lactobacillus* MRS broth was used for lactobacillus strains. The test compounds were added in 2-fold serial dilutions and the bacteria were added to a final concentration of 5×10$^5$ cfu/mL. All incubations unless specified otherwise were carried out at 24 or 48 h at 37° C. in an anaerobic chamber (Whitley DG250 workstation, Microbiology International, Frederick, Md.). *Corynebacterium* and *lactobacillus* species were incubated aerobically.

Inhibition of spores and toxins in exponential phase cells. *C. difficile* ATCC43255 was used for this assay. Colonies from an overnight culture were suspended in supplemented BHIS broth to a final concentration of ~10$^8$ cfu/mL. Serial 2-fold dilutions of the test compounds were prepared starting at 2- or 4-fold below the MIC and 2- or 4-fold above the MIC of the compound to a final volume of 10 mL and the bacteria were added to obtain a final concentration of 5×10$^5$ cfu/mL. The tubes were incubated anaerobically for 3 days. A 100-µl aliquot of the supernatant was removed every 24 h and stored at −80° C. for toxin analysis. For quantification of viable cells and spores additional 100-µL aliquots were removed and plated. Spores were quantified as reported earlier using ethanol treatment (Goldstein et al, *Anaerobe* 2010, 16(3), 220).

Toxin A and B detection. Total toxin A and B levels in the culture supernatant were measured using a commercial enzyme linked immunosorbent assay (ELISA) kit (Premier Toxins A and B, Meridian Bioscience Inc., Cincinnati, Ohio) according to the manufacturer's recommendations. Data were read at A$_{450}$ using ELISA plate reader (Epoch, BioTek instruments Inc., Winooski, Vt.).

Macromolecular synthesis assays. The method of Mathur et al (*J Antimicrob Chemother* 2011, 66(5), 1087) was used with a few modifications. [2,8-$^3$H]-adenine (40 Ci/mmol), 1-[3,4,5-$^3$H(N)]-leucine (120 Ci/mmol), and N-acetyl-d-[6-$^3$H]-glucosamine (30 Ci/mmol) were purchased from Perkin Elmer (Waltham, Mass.). Ciproflaxin, linezolid, and oxacillin, were used as positive controls for DNA, protein, and peptidoglycan, respectively. Ciprofloxacin and oxacillin were purchased from Sigma-Aldrich (St. Louis, Mo.), linezolid was obtained from AmplaChem Inc. (Carmel, Ind.). Radiolabeled precursors (final concentration of 1.0 µCi/mL for DNA and peptidoglycan and 2.0 µCi/mL for protein) were incubated with logarithmically growing *C. difficile* ATCC 43255 at 37° C., followed by addition of oxadiazole 2 at ½, 1, or 2× MIC, with further incubation for 180 min. Aliquots were taken every 30 min for radioactive counting and viability. Optimal incubation times were 60 min for DNA, 180 min for protein, and 120 min for peptidoglycan.

Animals. Female C57Bl/6J (8-9 weeks old) were purchased from Envigo Corp. (Huntington, United Kingdom) for the *C. diffcile* study. Female ICR mice (6-8 weeks old, ~20-g body weight) were used for the PK studies and purchased from Harlan Laboratories, Inc. (Indianapolis, Ind.). Mice were given Teklad 2019 Extruded Rodent Diet and water ad libitum. Mice were maintained in polycarbonate shoebox cages with ¼ in. corncob (The Andersons Inc., Maumee, Ohio) and Alpha-dri (Sheperd Specialty Papers, Inc., Richland, Mich.) bedding under 12-h light/12-h dark cycle at 72±2° F. All procedures involving vertebrate animals were approved by the Institutional Animal Care and Use Committee at the University of Notre Dame.

Pharmacokinetic (PK) Studies. Oxadiazole 2 was dissolved in 10% DMSO/25% Tween-80/65% water at a concentration of 5 mg/mL. Mice (n=3 per time point) were administered 100 µL (equivalent to 20 mg/kg) po by gastric intubation or intravenously (iv) by tail vein injection. Terminal blood was collected by cardiac puncture with sodium heparin at the following time points: 0.5, 1, 2, 3, 4, 6, 9, 24, 36 h for po administration and 2, 5, 10, 20, 40 min and 1, 2, 3, 4, 8, 24 h for iv administration. Whole blood was centrifuged at 1000 g for 10 min to obtain plasma. Aliquots of the plasma samples (50 µL) were analyzed the day of collection; the remaining plasma was stored at −80° C.

Plasma samples were analyzed by ultra-performance liquid chromatography (UPLC, Waters Corp., Milford, Mass.) coupled to a triple quadrupole mass spectrometer (TQD, Waters) operating in multiple reaction monitoring (MRM) mode. A standard curve of oxadiazole 2 was prepared in 50 µL of blank mouse plasma. Protein was precipitated by addition of 150 µL of acetonitrile containing internal standard. Samples were centrifuged at 22,000 g for 15 minutes, and the supernatants were analyzed by UPLC-MS/MS-MRM. Acquisition parameters were as follows: Supelco Ascentis C18 column (3 µm particle size, 10 cm×2.1 mm; Sigma-Aldrich, St. Louis, Mo.), electrospray ionization positive mode (ESI+), flow rate 0.5 mL/min, capillary voltage 4 kV, cone voltage 30 V, and collision voltage 25 V. The solvent program was as follows: 95% A-5% B for 0.25 min, 0.75-min linear gradient to 5% A-95% B, hold for 4 min, where A is 0.1% formic acid/water and B is 0.1% formic acid/acetonitrile. The method was linear between 0 µM and 20 µM ($R^2$ values 0.98-0.99). MRM transitions were 323.0→121.1 for oxadiazole 2 and 401.1→122.8 for the internal standard. Peak areas for oxadiazole 2 and the internal standard were calculated using Waters MassLynx software. A standard curve of peak area ratio to the internal standard plotted against standard concentration was generated from which concentrations of oxadiazole 2 in the plasma samples from the PK studies were determined using regression parameters.

Phoenix WinNonlin 6.3 (Certara LP, St Louis, Mo.) noncompartmental analysis using uniform weighing was used to calculate the area under the curve (AUC), clearance (CL), volume of distribution (Vd), and terminal half-life. Half-lives were estimated from the linear portion of the initial or terminal phases of the concentration-time data by linear regression, where the slope of the line was the rate constant k and $t_{1/2}$=ln 2/k.

Toxicity of Oxadiazole 2. Female uninfected C57Bl/6 mice (n=3) were given multiple po doses of oxadiazole 2 at 40 mg/kg once a day for 5 days. The oxadiazole was dissolved in 5% DMSO/25% Tween-80/70% water. Mice were clinically observed and body weights were recorded daily. Feces were collected daily and analyzed for concentrations of the oxadiazole by UPLC with MRM detection (see Table 3).

*C. difficile* Mouse Model. The model developed by Chen et al (*Gastroenterology* 2008, 135(6), 1984) was used with a few modifications. Mice (n=10/group) were treated with a mixture of kanamycin (0.4 mg/mL), gentamicin (0.035 mg/mL), colistin (850 U/mL), metronidazole (0.215 mg/mL), and vancomycin (0.045 mg/mL) added to the drinking water and supplemented with 5% sucrose for five days. After antibiotic treatment, the mice were given autoclaved water for 2 days. The following day, mice were administered a single 10 mg/kg intraperitoneal (ip) dose of clindamycin. One day later (day 0), the mice are infected with $10^4$ cfu of *C. difficile* strain VPI 10463 (ATCC 43255) intragastrically. One hour after infection, vancomycin (50 mg/kg/day oral (po)) or oxadiazole 2 (20 mg/kg/day po) was given for 5 days. A negative vehicle control will be included. Survival was recorded daily for 25 days and body weights were recorded 5 times a week. This study was conducted in duplicates.

A second study was conducted with oxadiazole 2 given po at 20 or 40 mg/kg for 5 days and vancomycin administered at 50 mg/kg po for 5 days. Fecal samples were collected on days 3, 7, and 10 for *C. difficile* spore and toxin evaluation.

Statistical Analyses. Data were analyzed for statistical significance using the Student t-test (Excel) using a two-tail distribution and unequal variance.

Summary. Novel oxadiazoles with activity against *C. difficile* are disclosed. Oxadiazole 2 has similar activity against NAP1/027 strains BAA-1870 and BAA-1803 as vancomycin; it inhibits not only vegetative cells, but spore and toxin production. The compound inhibits peptidoglycan synthesis, it is poorly absorbed, and it attains high concentrations in the gut. Oxadiazole 2 is well tolerated in mice and shows efficacy better than vancomycin in a mouse model of recurrent CDI.

Example 2

Pharmaceutical Dosage Forms

The following formulations illustrate representative pharmaceutical dosage forms that may be used for the therapeutic or prophylactic administration of a compound of a formula described herein, a compound specifically disclosed herein, or a pharmaceutically acceptable salt or solvate thereof (hereinafter referred to as 'Compound X'):

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |

| (ii) Tablet 2 | mg/tablet |
|---|---|
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Compound X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Compound X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Compound X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Compound X' | 5% |
| White bees wax | 10% |
| Liquid paraffin | 30% |
| Benzyl alcohol | 5% |
| Purified water | q.s. to 100 g |

| (xi) Topical Cream 2 | wt. % |
|---|---|
| 'Compound X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A method of treating a *Clostridium difficile* bacterial infection in a gastrointestinal tract of a subject comprising administering to a subject in need thereof an effective amount of compound 2:

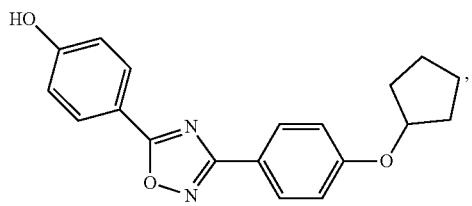

(2)

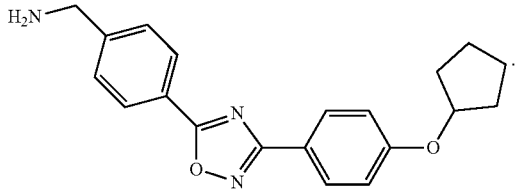

(viii)

or a salt thereof;
wherein the *Clostridium difficile* bacterial infection is located in the gastrointestinal tract of the subject and less than 30 percent of compound 2 is absorbed by the gastrointestinal tract, thereby treating the *Clostridium difficile* infection.

2. The method of claim 1 further comprising administering an agent capable of delaying absorption of the compound.

* * * * *

UNITED STATES PATENT AND TRADEMARK OFFICE
CERTIFICATE OF CORRECTION

PATENT NO. : 11,168,062 B2
APPLICATION NO. : 16/332311
DATED : November 9, 2021
INVENTOR(S) : Mayland Chang et al.

Page 1 of 1

It is certified that error appears in the above-identified patent and that said Letters Patent is hereby corrected as shown below:

In the Claims

• In Claim 1, at Column 40, Lines 2-10, please remove compound viii (both the structure and its label "viii"):

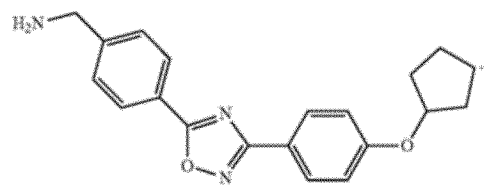

Signed and Sealed this
Thirty-first Day of May, 2022

Katherine Kelly Vidal
*Director of the United States Patent and Trademark Office*